(12) United States Patent
Fu et al.

(10) Patent No.: US 9,598,448 B2
(45) Date of Patent: Mar. 21, 2017

(54) OSMIUM (II) ARENE IMINO ANTI-CANCER COMPLEXES

(71) Applicant: University of Warwick, Coventry (GB)

(72) Inventors: Ying Fu, Coventry (GB); Peter John Sadler, Warwks (GB); Abraha Habtemariam, Edinburgh (GB)

(73) Assignee: University of Warwick, Coventry (GB)

( * ) Notice: Subject to any disclaimer, the term of this patent is extended or adjusted under 35 U.S.C. 154(b) by 0 days.

(21) Appl. No.: 15/066,830

(22) Filed: Mar. 10, 2016

(65) Prior Publication Data

US 2016/0272663 A1    Sep. 22, 2016

Related U.S. Application Data

(63) Continuation of application No. 13/642,729, filed as application No. PCT/GB2011/000591 on Apr. 15, 2011, now Pat. No. 9,296,772.

(30) Foreign Application Priority Data

Apr. 22, 2010 (GB) .................................. 1006762.7

(51) Int. Cl.
 *C07F 15/00* (2006.01)
 *A61K 31/555* (2006.01)

(52) U.S. Cl.
 CPC .................................. *C07F 15/002* (2013.01)

(58) Field of Classification Search
 None
 See application file for complete search history.

(56) References Cited

PUBLICATIONS

Schmid, et al., J. Med. Chem., 50:6343 (2007).*

\* cited by examiner

*Primary Examiner* — Michael Barker
(74) *Attorney, Agent, or Firm* — Nixon Peabody LLP; Linda B. Huber

(57) ABSTRACT

The present invention relates to the use of certain osmium containing complexes such as cytotoxic agents particularly for the treatment of cancer. There is also provided novel osmium containing complexes, as well as pharmaceutical formulations comprising such complexes.

11 Claims, 8 Drawing Sheets

(2)

(3*)

(5)

(8)

(11)

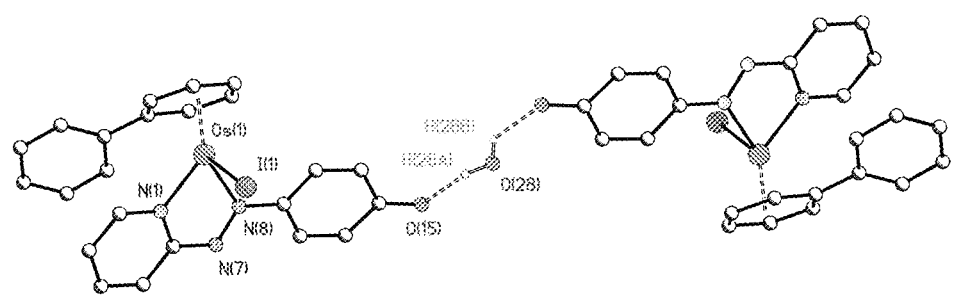
FIG. 4
FIG. 5A
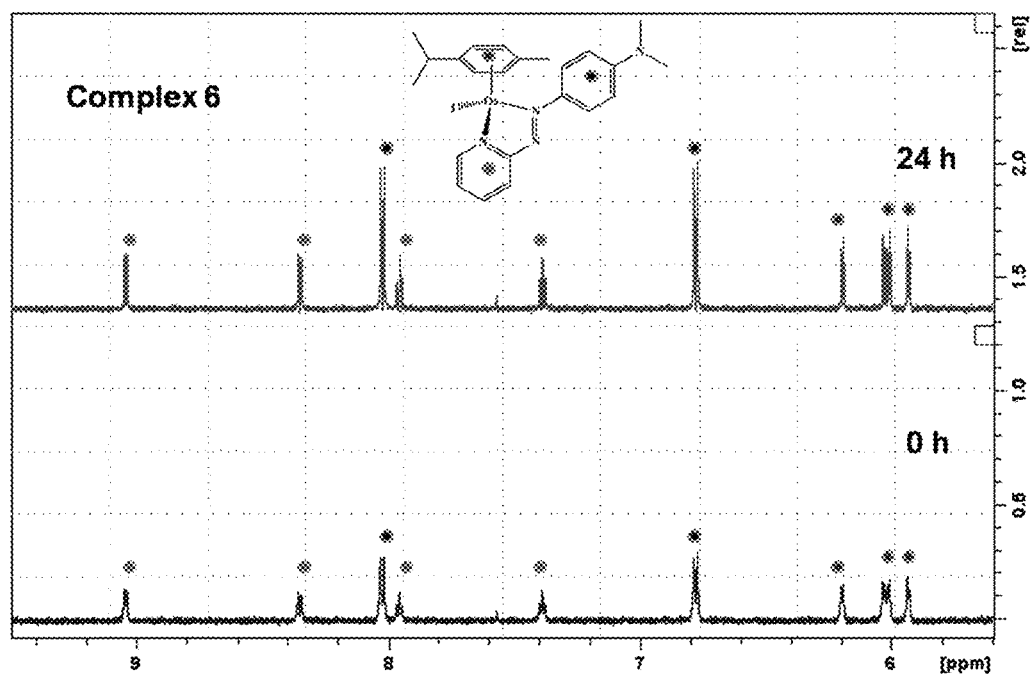

OSMIUM (II) ARENE IMINO ANTI-CANCER COMPLEXES

CROSS-REFERENCE TO RELATED APPLICATIONS

This application claims the benefit of priority under 35 U.S.C. §120 as a continuation of U.S. patent application Ser. No. 13/642,729 filed Oct. 22, 2012, which is the National Phase of International Application No. PCT/GB2011/000591 filed Apr. 15, 2011, which designated the U.S. and that International Application was published under PCT Article 21(2) in English, which also includes a claim of priority under 35 U.S.C. §119(a) and §365(b) to British patent application No. GB 1006762.7 filed Apr. 22, 2010, the entirety of which is hereby incorporated by reference.

FIELD OF THE INVENTION

The present invention relates to the use of certain osmium containing complexes such as cytotoxic agents particularly for the treatment of cancer. There is also provided novel osmium containing complexes, as well as pharmaceutical formulations comprising such complexes.

BACKGROUND TO THE INVENTION

The success of platinum complexes such as cisplatin and carboplatin as anticancer drugs is well known but these have a limited spectrum of activity, can have toxic side-effects and platinum-resistant tumours can develop.[1] For these reasons it is worthwhile to investigate the design of anti-cancer drugs based on other transition metals. Recently two octahedral $Ru^{III}$ complexes have entered clinical trials.[2,3] The $Ru^{III}$ complexes are thought to be reduced to active $Ru^{II}$ species in vivo. $Ru^{II}$ can be stabilized by π-bonded arene ligands and a range of $Ru^{II}$ arene complexes of the type [($\eta^6$-arene)Ru(XY)Z)] where XY=chelated diamine, Z=Cl show anticancer activity both in vitro and in vivo.[4,5] These complexes can undergo activation via hydrolysis and bind strongly to DNA, a potential target. Arene complexes of the heavier congener $Os^{II}$ can have almost identical geometries to those of $Ru^{II}$ but are subtly different. For example $Os^{II}$ chlorido complexes hydrolyse ca. 40× more slowly and the related aqua adducts have $pK_a$ values for Os—$OH_2$ which are ca. 1.5 pKa units lower (more acidic) than those of the analogous $Ru^{II}$ complexes. Although $Os^{II}$ arene complexes have now been reported which exhibit cancer cell cytotoxicity,[8,7] in general they are less potent than Ru arene complexes.

Recently, certain osmium complexes which comprise azopyridine ligand were developed[8]. However, the two compounds [($\eta^6$-p-cymene)Os(Azpy-NMe$_2$)Cl]PF$_6$ and [($\eta^6$-bip)Os(Azpy-NMe$_2$)Cl]PF$_6$ displayed poor solubility in water and did not show significant cytotoxicity against the A549 cancer cell line. Although some of the iminopyridine ligands used in the present invention have been reported and used in metal coordination complexes, the only previous report of an osmium arene complex is that of Schmid et al (complex 4b in J Med Chem 2007, 50, 6343-6355) for a specific Paullone derivative which is active against A549, CH1 and SW480. The present invention shows that the nature of the iminopyridine can have unexpected effects on cancer cell cytotoxicity.

Organometallic 2005, 24, 8, 1966-1973 reports on an osmium complex comprising a 2,2'-azopyridine ligand, but there is no disclosure of any pharmaceutical activity.

SUMMARY OF THE INVENTION

The present invention is based on the development of further osmium containing azo and imino complexes and their potential use as cytotoxic agents, especially as anticancer agents.

Thus, in a first aspect there is provided a compound formula (I) for use as a cytotoxic agent, especially an anticancer agent, or as an immunosuppression agent:

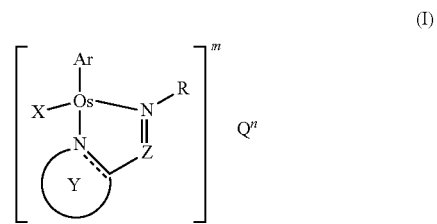

(I)

or a dinuclear or polynuclear form thereof, wherein
Ar is an arene moiety;
X is halo, or a donor ligand;
Y represents, a cyclic or bicyclic ring structure, such as a three, four, five, six, seven or eight-membered saturated or unsaturated heterocyclic ring, which may be optionally substituted at one or more positions on the ring(s) and where the dashed line represents and optional double bond;
Z is N or CR', where R' may be H, CN, $N_3$, $C_1$-$C_{10}$ alkyl or aryl;
R is a substituted or unsubstituted cyclic or heterocyclic ring, such as a five or six membered, or a chain, such as a substituted or unsubstituted $C_1$-$C_{10}$ alkyl, $C_2$-$C_{10}$ akenyl or $C_2$-$C_{10}$ alkyl, optionally the ring may be separated from the nitrogen to which it is attached, by a spacer group, such as a $C_1$-$C_4$ alkyl;
Q is an ion and is either present or absent;
m and n are charges, independently either absent or selected from a positive or negative whole member, or solvates or prodrugs thereof and physiologically active derivatives thereof.

In a second aspect there is also provided a pharmaceutical composition comprising a compound according to formula (I) as defined above in relation to the first aspect, together with a pharmaceutically acceptable carrier thereof.

In a third aspect the present invention also relates to novel compounds according to formula (I) as defined above in relation to the first aspect, excluding the compounds: [($\eta^6$-p-cymene)Os(Azpy-NMe$_2$)Cl]PF$_6$, [($\eta^6$-bip)Os(Azpy-NMe$_2$)Cl]PF$_6$, and (abpy)OsCl(C$_6$Me$_6$)PF$_6$ In a further aspect, the present invention provides a method of treatment or prophylaxis of a disease involving abnormal cell proliferation, such as a cancer, said method comprising administering a therapeutically or prophylactically useful amount of a compound according to the first aspect of the present invention, optimally excluding compounds: [($\eta^6$-p-cymene)Os(Azpy-NMe$_2$)Cl]PF$_6$ and [($\eta^6$-bip)Os(Azpy-NMe$_2$)Cl]PF$_6$.

There is also provided use of a compound as defined herein in the manufacture of a medicament for use in treating a proliferative disease, such as cancer, or for use in immunosuppression.

The unsaturated or saturated ring Y may be substituted with one or more groups or fused or otherwise substituted to one or more further unsaturated or saturated rings, which may or may not be heterocyclic. Suitable substituents include $C_1$-$C_4$ alkyl, OH, $NH_2$, $NO_2$, and halo, such as I, Cl, or Br. The substituent may also be a peptide, such as an oligo-arginine peptide comprising 4-9, such as 6-8 linearly repeating arginine groups. Evidence from other Osmium arene anticancer complexes (Bioconjugate Chemistry, 2011, 22, 218-226), to which the skilled reader is directed has shown that conjugating peptides, such as oligo-arginine peptides, in this manner can have an effect on cellular uptake, internalisation and/or cytotoxicity. Optionally the ring structure Y may include one or more further heteroatoms in the ring Y or the rings fused therewith.

Preferred Y ring structures are saturated N-containing five or six membered rings, such as a pyridine ring.

Preferably Z is N or CH.

R is preferably an unsubstituted or substituted phenyl, when substituted, the phenyl group may be substituted on one or more carbons in the ring by $C_1$-$C_4$ alkyl, OH, amino or substituted amino, e.g. dialkylamino, such as dimethylamino, carboxylate or substituted carboxylate, e.g. an ester, ether or polyether, nitro, halo, trifluoromethyl.

R itself can also be heterocyclic ring e.g. pyridine

Substitutents on R could be another ring e.g. phenyl or substituted phenyl, 5- or 6-membered heterocyclic ring.

Preferably X is I.

In a preferred embodiment, the compounds as defined in the first, second and third aspects are according to formula II,

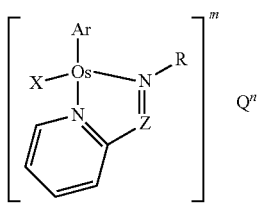

(II)

wherein the substituents Ar, X and R are as previously defined above. Preferably X is I and/or R is a substituted or unsubstituted phenyl (as previously defined), or $C_1$-$C_4$ alkylphenyl In a further preferred embodiment, the compounds as defined in the first, second and third aspects are according to formula (III)

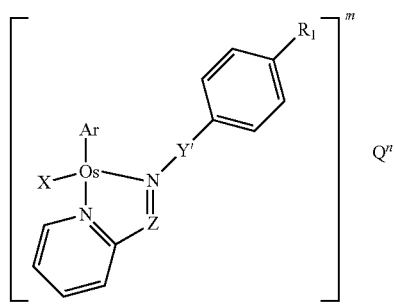

(III)

wherein the substituents X and Ar, are previously as defined and Z is N or CH, $R_1$ is H, $C_1$-$C_4$ alkyl, OH, amino or substituted amino, e.g. dialkylamino, such as dimethylamino, carboxylate or substituted carboxylate, e.g. an ester, ether or polyether, nitro, halo, trifluoromethyl, or could be another ring e.g. phenyl or substituted phenyl, 5- or 6-membered heterocyclic ring; Y' is absent or a C(R')(R") group wherein, R' is H and R" is $CH_3$ or vise versa.

Substitutents can be attached to this position for the purpose of modifying stability, solubility, selectivity and targeting (e.g. using peptides)

Most preferred compounds are in accordance with formula (III), wherein Z is N or CH, X is I, $R_1$ is OH, or $N(CH_3)_2$, R' and R" are independently an H or methyl group. and Q is $PF_6$ or another negatively charged counter ion as defined herein.

The arene group (Ar), may be any arene, which may be substituted or unsubstituted. Exemplar structures are a benzene ring which may be optionally substituted by a branched or unbranched substituted or unsubstituted linear or cyclic alkyl, branched or unbranched substituted or unsubstituted linear or cyclic alkenyl, branched or unbranched substituted or unsubstituted linear or cyclic alkynyl or substituted or unsubstituted monocyclic or polycyclic aryl or heteroaryl, carboxy, alkyloxycarbonyl hydroxyl, amino, nitro, alkyloxy, alkylthio, formyl, cyano, carbamoyl, halo (e.g. fluoro, chloro, bromo or iodo), —$S(O)NR^{12}R^{13}$ or —$S(O)R^{14}$.

Examples of arene groups include benzene, naphthalene, anthracene, phenanthrene, fluoranthene, pyrene, triphenylene, fluorene, indene and the like. Other examples of suitable arene groups include biphenyl, cumene, styrene, mesitylene, cymene, toluene, xylene and the like. Yet further arene groups include partially hydro arene groups such as dihydro-naphthalene ($C_{10}H_{10}$), dihydro-anthracene, tetrahydroanthracene and the like. Preferred arenes are biphenyl and cymene, with biphenyl most preferred.

The present invention also extends to compounds in which the arene group is tethered to the ligand moiety. The tether may be attached to the ligand at any position, including for example substituents or ring groups on the ligand.

For example, in compounds having the structure (I) above, the tether may be attached to a carbon atom of the ring Y.

Tethers may also be used to provide dinuclear and polynuclear complexes comprising at least one Os(II). All of the metal atoms present may be Os(II) or alternatively, metals in addition to the at least one Os(II) (e.g. other group VIII transition metals in the periodic table) may be chosen thus providing polyheteronuclear complexes.

Typically, in such compounds the other metal is Ru(II), or Pt(IV).

In such dinuclear and polynuclear complexes, the tethers may bridge between each of the complexes in any of a number of independent ways. For example, the tether may form a linkage between any one of the arene (Ar), or the Y or R groups, directly from the Os in a first complex molecule to any one of those same positions in a second complex molecule, which is thereby joined or tethered to the first molecule.

Di- or polynuclear complexes containing both Os(II) and Ru(II) may be advantageous due to the differing properties and reactivities of the respective tethered Os(II) and Ru(II) complexes.

The tethers may be selected from any suitable group to provide a link between the respective desired groups of the complexes to be joined.

Typical tethers may be selected from alkylene, alkenylene, alkynylene, aromatic-containing groups, wherein the aromatic groups may optionally contain heteroatoms; and heteroatom-containing groups such as peptide, ester and ether linkages.

The group X in the compounds according to formula (I) may be selected from the halogens i.e. fluoro, chloro, bromo or iodo, particularly chloro and iodo. Alternatively, the group X may be selected from any suitable donor ligand, examples of which are ligands wherein the donor atom thereof is selected from the group consisting of nitrogen, oxygen, sulphur or phosphorus.

Typically, such ligand groups may be selected from pyridine (and derivatives thereof), water, hydroxo (i.e. OH$^-$), azides or pseudohalogens and the like.

The group X may be replaced by other groups when the compounds described herein are presented in a biological environment, for example, the species wherein X is water or hydroxo may be formed in a biological environment.

The ion, Q in compound according to formula (I), acts as a counter ion to the complex and balances the charges in the complex to generally provide a molecular species with overall charge of zero.

Negatively charged counter ions may be any suitable ion, for example selected from $BF_4$, $BPh_4$, $PF_6$, triflate, trisphat and halides.

Positively charged counter ions may be any suitable ion, for example alkali metal cations such as $Na^+$ and $K^+$, or alkaline earth metal cations such as $Mg^{2+}$ and $Ca^{2+}$. Positive counter ions may also include organic cations, other metal complexes, protonated heterocyclic compounds and substituted or unsubstituted ammonium ions, i.e. $NH_4^+$.

The counter ion may be chosen for certain purposes, for example, non-nucleophilic anions may be preferred, such as $BPh_4$ which tends to provide an insoluble complex thereby providing a useful advantage during a recovery stage of the compound preparation, e.g. for separation out of a solution or liquid medium. $PF_6$ may have a similar effect by providing a complex which is more soluble than a corresponding complex with $BPh_4$ counter ion, whilst remaining less soluble than a corresponding complex with chloride as the counter ion. These counter ions are not, however, necessarily excluded from the compound in its final useable form.

The counter ions may be chosen to provide a useful solubility for preparation of the complexes and the same counter ion may be retained or exchanged for another counter ion to provide a compound better suited for pharmaceutical/medical uses.

For example, triflate may be selected, or chloride, bromide or iodide to provide more easily soluble compounds.

Physiologically functional derivatives of compounds of the present invention are derivatives which can be converted in the body into the parent compound. Such physiologically functional derivatives may also be referred to as "pro-drugs" or "bioprecursors". Physiologically functional derivatives of compounds of the present invention include in vivo hydrolysable esters. Additionally, the compounds of the present invention, may themselves, be considered as pro-drugs, which are converted into a physiologically active form in the body. Examples are the water (or aqua) complexes, i.e. where X is $H_2O$, which, without wishing to be bound by theory, are thought to be the active species in the biological environment.

It may be convenient or desirable to prepare, purify, and/or handle a corresponding solvate of the compounds described herein, which may be used in any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds recited herein, as well as wholly or partially racemic mixtures of such enantiomers.

The compounds of the present invention may be prepared using reagents and techniques readily available in the art and as described hereinafter. Novel intermediate compounds in the synthetic route for preparation of the compounds of the present invention may be important molecules for general application for the preparation of the molecules of the present invention. Accordingly, the present invention extends to include those novel intermediate compounds.

The present invention also extends to the methods of preparing the compounds described herein. Generally, the method comprises providing a compound of formula $[ArOsX_2]_2$ in a first step and then reacting the compound with the azo or imino containing ligand such as azopyridine or iminopyridine containing ligands in a second step to provide a compound according to formula (I).

The groups Ar and X have the same meaning as hereinbefore recited.

Preferably, in the preparation X in the starting material is halo, such as chloro or iodo.

During the preparation, a step may be included to exchange the counter ion of the complex for a different preferred counter ion.

Preferred preparation conditions comprise i) providing and dissolving the compound $[ArOsX_2]_2$ with the ligand/ligand precursor in an alcoholic solvent, such as methanol, which may include an amount of water, optionally heating or refluxing the solution with or without stirring and for an amount of time as may be determined by the skilled addressee;

ii) introducing a suitable compound to the resultant mixture to add a preferred counter ion to the formed complex.

For example, a suitable compound for introducing the counter ion $PF_6$, is $NH_4PF_6$.

As indicated above, the present invention provides a treatment or prophylaxis of a disease, pathology or condition recited herein comprising administering a compound recited herein to a patient in need thereof.

Diseases involving abnormal proliferation of cells are treatable with the compounds recited herein. Examples of such diseases include cancers and hyperproliferation disorders.

Examples of cancers which may be treated by the active compounds include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma. Particularly preferred cancers may include leukemia, colon cancer, melanoma and breast cancer.

Without wishing to be bound by theory, present evidence suggests that the compounds of the present invention may function as tubulin inhibitors. Not only does this strengthen and support their utility as anti-cancer agents, but it supports their use in treating other diseased associated with unwarranted cellular proliferation, as well as potential immunosuppressive agents, which may find application in preventing the rejection of transplanted organs and tissues (e.g., bone marrow, heart, kidney, liver), treating for example, autoimmune diseases or diseases that are most likely of autoimmune origin (e.g., rheumatoid arthritis, multiple sclerosis, myasthenia gravis, systemic lupus erythematosus, focal segmental glomerulosclerosis, Crohn's disease, Behcet's Disease, pemphigus, and ulcerative colitis) and treating some other non-autoimmune inflammatory diseases (e.g., long term allergic asthma control).

Examples of other therapeutic agents that may be administered together (whether concurrently or at different time intervals) with the compounds of the formula (I) include but are not limited to topoisomerase inhibitors, alkylating agents, antimetabolites, DNA binders and microtubule inhibitors (tubulin target agents), such as cisplatin, cyclophosphamide, doxorubicin, irinotecan, fludarabine, 5FU, taxanes, mitomycin C or radiotherapy. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where the compound of the formula (I) is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

The patient is typically an animal, e.g a mammal, especially a human.

For use according to the present invention, the compounds or physiologically acceptable salt, ester or other physiologically functional derivative thereof described herein may be presented as a pharmaceutical formulation, comprising the compound or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Advantageously, solutions may be prepared and stored in a ready to use condition, (e.g. without the need for further formulation such as dilution into a useable concentration), in light-excluding containers such as sealed bottles, ampoules, blister packages and the like. Such containers are preferably provided in a sterile condition.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline.

Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

Embodiments of the present invention shall now be described with reference to the following non-limiting figure examples and the Tables, in which:

FIG. 4 shows schematically hydrogen bond formation between water and a phenoxide ligand on a complex of the present invention;

FIGS. 5A-5C, 6 and 7 show the hydrolysis and stability study of complexes 6, 8 and 12.

Figure 8:
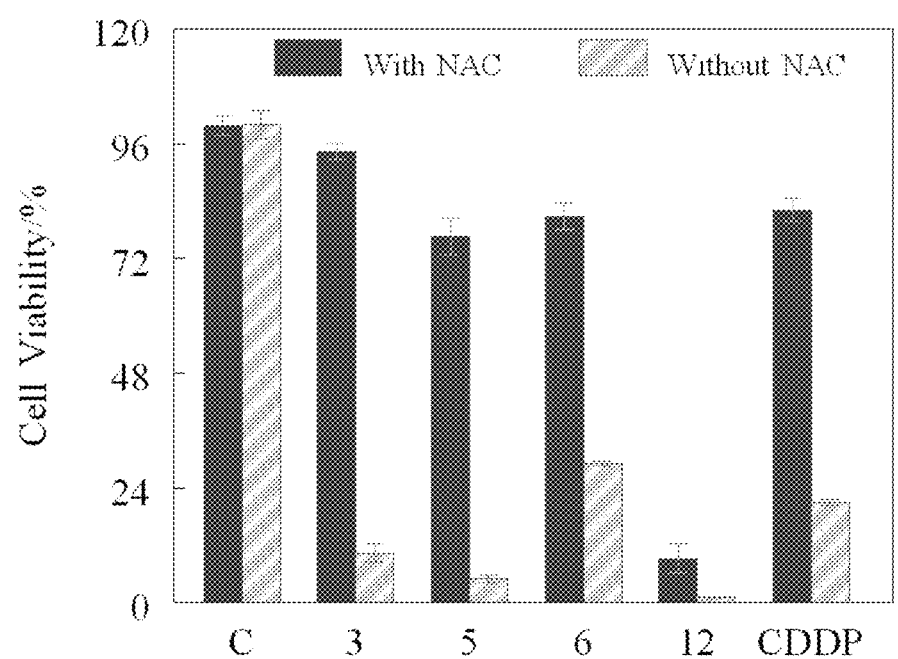
Figure 9:
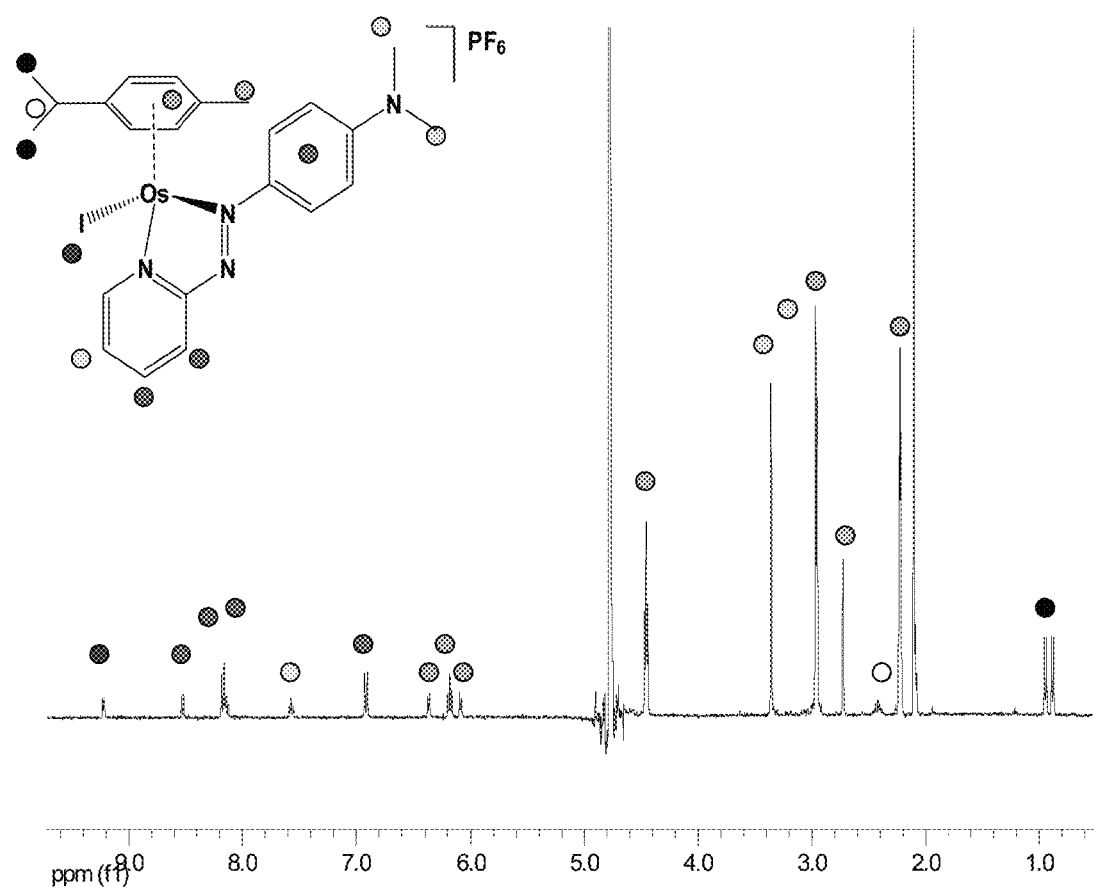

FIG. 8 shows the results of cell viability assays of cells with/without N-acetyl-L-cysteine (NAC) treatment prior to and together with administering compounds encoding to the present invention;

FIG. 9 shows the study of complex 6 with NAC; and

Figure 10:
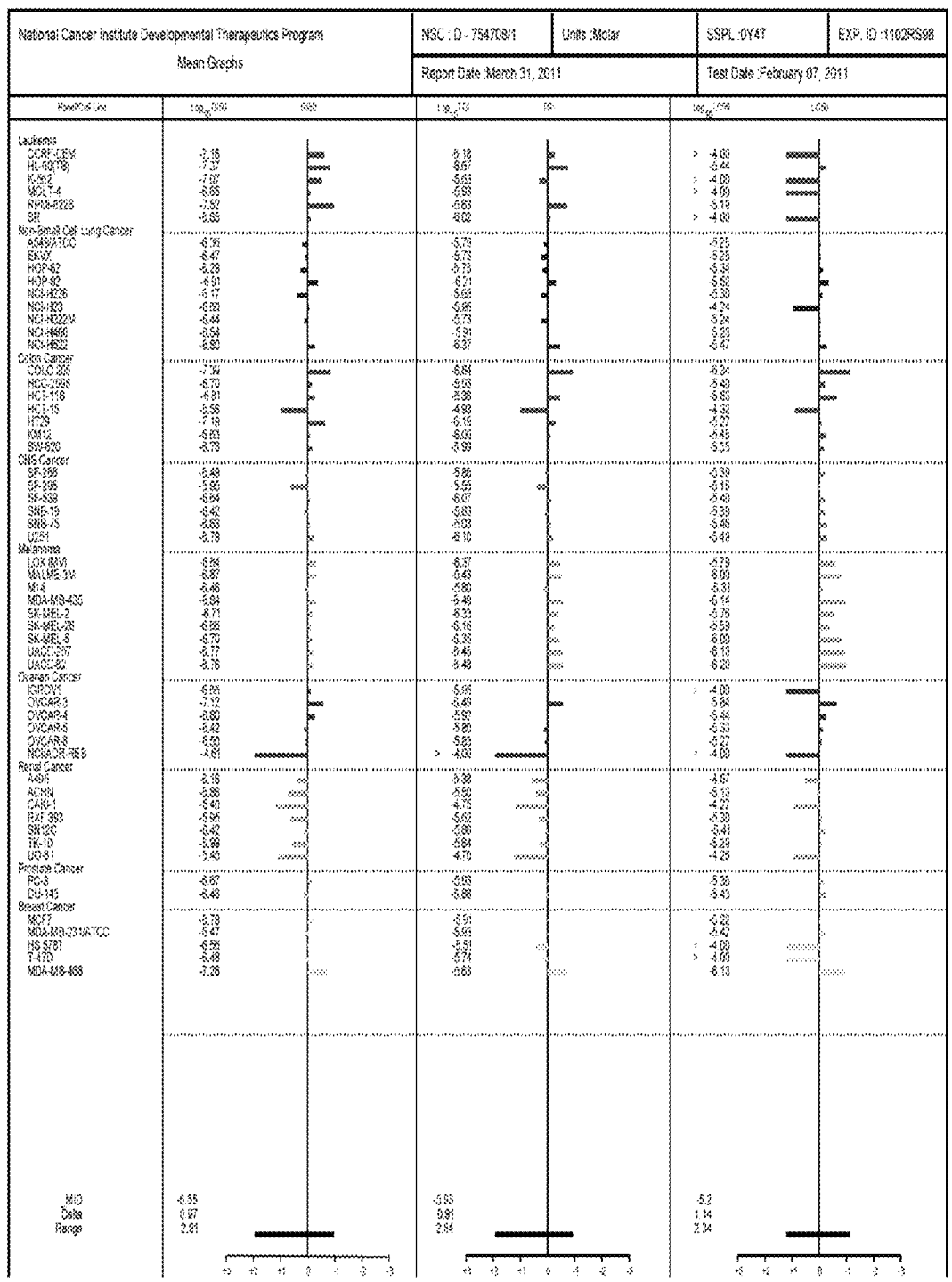

FIG. 10 shows $IC_{50}$ and COMPARE analysis of a compound of the present invention against a variety of cell lines Table 1 shows the $IC_{50}$ values of compounds according to the present invention;

Table 2 shows the selected bond lengths of X-ray structures of compound according to the present invention

EXPERIMENTAL SECTION

Synthesis.

Complexes [($\eta^6$-bip)Os(Azpy)I]PF$_6$ (1), [($\eta^6$-p-cym)Os (Azpy)I]PF$_6$ (2), [($\eta^6$-bip)Os(Azpy-OH)I]PF$_6$ (3), [($\eta^6$-p-cym)Os(Azpy-OH)I]PF$_6$ (4), [($\eta^6$-bip)Os(azpy-NMe$_2$)I]PF$_6$ (5), [($\eta^6$-p-cym)Os(Azpy-NMe$_2$)I]PF$_6$ (6), [($\eta^6$-bip)Os (Azpy)Cl]PF$_6$ (7), [($\eta^6$-p-cym)Os(Azpy)Cl]PF$_6$ (8), [($\eta^6$-bip)Os(azpy-OH)Cl]PF$_6$ (9), [($\eta^6$-p-cym)Os(Azpy-OH)Cl] PF$_6$ (10), [($\eta^6$-bip)Os(azpy-NMe$_2$)Cl]PF$_6$ (11), an d[($\eta^6$-p-cym)Os(Azpy-NMe$_2$)Cl]PF$_6$ (12) were prepared with purities of >95% by reacting the appropriate azopyridine derivative with [($\eta^6$-bip)OsCl$_2$]$_2$, [($\eta^6$-bip)OsI$_2$]$_2$, [($\eta^6$-p-cym)OsCl$_2$]$_2$ or [($\eta^6$-p-cym)OsI$_2$]$_2$, as described below. Complexes 13-16 were synthesized by a similar procedure but using the appropriate iminopyridine ligand as described below.

Materials.

OsCl$_3$.3H$_2$O and 4-(2-pyridylazo)-N,N-dimethylaniline (Azpy-NMe$_2$) were purchased from Alfa-Aesar. Ethanol and methanol were dried over Mg/I$_2$ or anhydrous quality was used (Aldrich). All other reagents used were obtained from commercial suppliers and used as received. Azpy-OH was a gift from Dr. Sarah Dougan. The preparation of the starting materials [($\eta^6$-bip)OsCl$_2$]$_2$ and [($\eta^6$-p-cym)OsCl$_2$]$_2$ were based on a literature report.[8] The A2780 human ovarian carcinoma cell line was purchased from European Collection of Cell Cultures, RPMI-1640 media and trypsin from Invitrogen, bovine serum was from Biosera, penicillin, streptomycin, TCA and SRB from Sigma-Aldrich, and tris [hydroxymethyl]aminomethane from Formedium.

Synthesis of Azo Ligands.

Syntheses of azpy was based on literature reports.[9]

Synthesis of Complexes

[($\eta^6$-bip)OsI$_2$]$_2$

The dimer [($\eta^6$-bip)OsCl$_2$]$_2$ (100.4 mg, 0.12 mmol) was stirred at 353 K for 1 h suspended in water (200 mL). The solution was then hot-filtered and KI (1039.8 mg, 6.26 mmol) was added to the solution. A deep orange precipitate was formed immediately. The solution was left at 277 K for 2 h. The precipitate was collected by filtration and washed with cold ethanol and diethyl ether, then dried in a desiccator overnight. Yield: 95.4 mg (66.0%). Anal. $^1$H NMR (DMSO-d$_6$) δ 7.74 (d, 4H, J=8 Hz), 7.45 (m, 6H), 6.84 (d, 4H, J=6 Hz), 6.56 (t, 2H, J=6 Hz), 6.34 (t, 4H, J=6 Hz). CHN analysis. Found C, 24.33%; H, 1.64%, Calcd for C$_{24}$H$_{20}$I$_4$Os$_2$: C, 24.09%; H, 1.68%.

[($\eta^6$-p-cym)OsI$_2$]$_2$

The dimer [($\eta^6$-p-cym)OsCl$_2$]$_2$ (103.8 mg, 0.135 mmol) was stirred at 353 K for 1 h to allow it to dissolve in water (50 mL). Then KI (2683.9 mg, 16.18 mmol) was added to the solution and heated under reflux for 1 h. A deep orange precipitate was formed immediately. The solution was left at 277 K for 2 h. The precipitate was collected by filtration and washed with little cold ethanol and diethyl ether, then dried in a desiccator overnight. Yield: 112.6 mg (67.9%). Anal. $^1$H NMR (DMSO-d$_6$) δ 6.10 (d of d, 8H), 3.04 (m, 2H), 2.43 (s, 6H), 1.25 (d, 12H, J=8 Hz). CHN analysis. Found: C, 20.78%; H, 2.35%, Calcd for C$_{20}$H$_{28}$I$_4$Os: C, 20.77%; H, 2.44%.

[($\eta^6$-bip)Os(Azpy)I]PF$_6$ (1)

[($\eta^6$-bip)OsI$_2$]$_2$ (30 mg, 0.025 mmol) in methanol (30 mL) and water (10 mL) was heated under reflux at 353 K under nitrogen for 2 h. Azpy (9.15 mg, 0.05 mmol) in methanol (10 mL) was added drop-wise. The solution-colour changed from orange to red immediately. After heating under reflux for a further 2 h; the solution was hot-filtered and the volume was reduced to about 10 mL on a rotary evaporator. Ammonium hexafluorophosphate (40.0 mg. 0.25 mmol) was added. The solution was left at 277 K for 2 h. A brown powder precipitated out. The powder was collected by filtration and washed with little cold ethanol and diethyl ether, then dried in a desiccator overnight. Yield: 20 mg (61.1%). Anal. ESI-MS Calcd for C$_{23}$H$_{19}$IN$_3$Os: m/z 656.0. found 655.9. $^1$H NMR ((CD$_3$)$_2$CO) δ 9.44 (d, 1H, J=8 Hz), 9.01 (d, 1H, J=8 Hz), 8.38 (t, 1H, J=8 Hz), 7.98 (d, 2H, J=8 Hz), 7.76 (m, 3H), 7.47 (m, 6H), 7.12 (d, 1H, J=6 Hz), 6.98 (t, 1H, J=6 Hz), 6.83 (m, 2H), 6.72 (t, 1H, J=5 Hz). CHN analysis Found: C, 35.41%; H, 2.40%; N, 5.55%, Calcd for C$_{23}$H$_{19}$F$_6$IN$_3$OsP: C, 34.55%; H, 2.40%; N, 5.26%.

[($\eta^6$-p-cym)Os(Azpy)I]PF$_6$ (2)

[($\eta^6$-p-cym)OsI$_2$]$_2$ (30.5 mg, 0.0264 mmol) was dissolved in methanol (20 mL) and Azpy (9.6 mg, 0.053 mmol) in methanol (10 mL) was added drop-wise. The solution-colour changed from yellow to brown gradually and was stirred at ambient temperature for 3 h. The volume was reduced to about 10 mL by removal of methanol on a rotary evaporator. Ammonium hexafluorophosphate (17.7 mg. 0.11 mmol) was added. Then the solution was left at 253 K for 24 h; a dark coloured powder precipitated, which was collected by filtration and washed with cold ethanol and diethyl ether, then finally dried in vacuum. Yield: 14.5 mg (35.3%). Anal. Calcd for C$_{21}$H$_{23}$IN$_3$Os: m/z 636.1. found 636.0. $^1$H NMR ((CD$_3$)$_2$CO) δ 9.66 (d, 1H, J=6 Hz), 9.04 (d, 1H, J=8 Hz), 8.41 (t, 1H, J=8 Hz), 8.20-8.19 (m, 2H), 7.87-7.75 (m, 4H), 6.77 (d, 1H, J=6 Hz), 6.43 (d, 1H, J=6 Hz), 6.38 (d, 1H, J=5 Hz), 6.32 (d, 1H, J=5 Hz), 2.67 (s, 3H), 2.62 (m, 1H), 1.02 (d of d, 6H). CHN analysis Found: C, 32.19%; H, 2.85%; N, 5.34%, Calcd for C$_{21}$H$_{23}$F$_6$IN$_3$OsP: C, 32.36%; H, 2.97%; N, 5.39%. Single crystals suitable for X-ray diffraction were obtained by slow evaporation of a methanol solution of complex 2 at ambient temperature.

[($\eta^6$-bip)Os(Azpy-OH)I]PF$_6$ (3)

[($\eta^6$-bip)OsI$_2$]$_2$ (86.1 mg, 0.072 mmol) in methanol (30 mL) and water (10 mL) mixture was heated under reflux at 353 K under nitrogen for 2 h. Azpy-OH (19.0 mg, 0.096 mmol) in methanol (10 mL) was added drop-wise, the solution colour changed from orange to red immediately, the solution was heated to reflux for a further 2 h, hot-filtered, and the volume was reduced to about 10 mL by removal of methanol on a rotary evaporator. Ammonium hexafluorophosphate (118.5 mg, 0.73 mmol) was added and the solution was left at 277 K for 2 h. A deep brown powder precipitated which was filtered off and washed with cold ethanol and diethyl ether, then dried in a desiccator overnight. Yield: 63.1 mg (53.7%). Anal. ESI-MS Calcd for C$_{23}$H$_{19}$IN$_4$OOs: m/z 672.02. found 671.9. $^1$H NMR ((CD$_3$)$_2$CO) δ 9.30 (d, 1H, J=9 Hz), 8.80 (d, 1H, J=8 Hz), 8.31-9.27 (m, 1H), 8.02 (d, 2H, J=9 Hz), 7.66-7.63 (m, 1H), 7.46 (m, 5H), 7.01 (d, 1H, J=6 Hz), 6.93 (d, 2H, J=6 Hz), 6.82 (m, 2H), 6.72 (t, 1H, J=6 Hz), 6.66 (d, 1H, J=6 Hz). CHN analysis Found: C, 34.07%; H, 2.34%; N, 5.03%, Calcd for C$_{23}$H$_{19}$F$_6$IN$_4$OOsP: C, 33.87%; H, 2.34%; N, 5.03%. Single crystals of [($\eta^6$-bip)Os(Azpy-O)I].0.5H$_2$O (3*) suitable for X-ray diffraction were obtained by slow evaporation of a methanol solution of complex 3 at ambient temperature.

[($\eta^6$-p-cym)Os(Azpy-OH)I]PF$_6$ (4)

[($\eta^6$-p-cym)OsI$_2$]$_2$ (50.5 mg, 0.0437 mmol) was dissolved in methanol (50 mL); Azpy-OH (17.4 mg, 0.087 mmol) in methanol (10 mL) was added drop-wise. The solution was stirred at ambient temperature for 24 h with 10 drops of 1 M HCl solution. The volume was reduced to about 2 mL by removal of methanol on a rotary evaporator. The complex was purified by chromatography on a Sephadex LH20 column. Ammonium hexafluorophosphate (28.6 mg. 0.18 mmol) was added. Then the solution was left at 277 K for 0.5 h. A dark coloured powder precipitated out, which was collected by filtration and washed with cold ethanol and diethyl ether, then finally dried in vacuum. Yield: 30.6 mg (43.2%). Anal. ESI-MS Calcd for $C_{21}H_{23}IN_3Os$: m/z 652.1. found 652.0. $^1$H NMR ((CD$_3$)$_2$CO) δ 9.75 (bs, 1H), 9.58 (d, 1H, J=6 Hz), 9.93 (d, 1H, J=8 Hz), 8.40-8.38 (m, 1H), 8.19 (d, 2H, J=9 Hz), 7.83-7.82 (m, 1H), 7.15 (d, 2H, J=9 Hz), 6.72 (d, 1H, J=6 Hz), 6.43 (m, 2H), 6.34 (d, 1H, J=6 Hz), 3.35 (s, 3H), 2.63 (m, 1H), 1.00 (d of d, 6H). CHN analysis Found: C, 31.04%; H, 3.05%; N, 5.28%, Calcd for $C_{21}H_{23}F_6IN_3OOsP$: C, 31.71%; H, 2.91%; N, 5.28%.

[($\eta^6$-bip)Os(azpy-NMe$_2$)I]PF$_6$ (5)

[($\eta^6$-bip)OsI$_2$]$_2$ (100 mg, 0.037 mmol) in methanol (30 mL) and water (10 mL) was heated under reflux at 348 K under nitrogen for 2 h. Azpy-NMe$_2$ (37.9 mg, 0.074 mmol) in methanol (10 mL) was then added drop-wise, the solution colour changed from orange to dark red immediately, then gradually turned to deep blue. It was further heated to reflux for 1 h, hot-filtered and the volume was reduced to about 10 mL by removal of methanol on a rotary evaporator, and ammonium hexafluorophosphate (135.1 mg. 0.37 mmol) was added. Then the solution was left at 277 K for 1 h. A dark colour powder precipitated and was collected by filtration, washed with cold ethanol and diethyl ether, then dried under vacuum. Yield: 22 mg (42.6%). Anal. ESI-MS Calcd for $C_{25}H_{24}IN_4Os$: m/z 699.07. found 699.0, $^1$H NMR ((CD$_3$)$_2$CO) δ 9.12 (d, 1H, J=6 Hz), 8.54 (d, 2H, J=8 Hz), 8.14 (m, 3H), 7.49-7.40 (m, 6H), 7.02 (d, 1H, J=6 Hz), 6.82 (d, 2H), 6.77 (d, 1H), 6.75-6.67 (m, 2H), 3.40 (s, 6H). CHN analysis Found: C, 36.22%; H, 2.93%; N, 6.81%, Calcd for $C_{25}H_{24}F_6IN_4OsP$: C, 35.65%; H, 2.87%; N, 6.65%. Single crystals of suitable for X-ray diffraction were obtained by slow evaporation of a methanol solution of complex 5 at ambient temperature.

[($\eta^6$-p-cym)Os(Azpy-NMe$_2$)I]PF$_6$ (6)

[($\eta^6$-p-cym)OsI$_2$]$_2$ (100.0 mg, 0.086 mmol) was dissolved in methanol (50 mL) at 313 K; Azpy-NMe$_2$ (39.5 mg, 0.175 mmol) in methanol (10 mL) was added drop-wise, the solution-colour changed from orange to blue immediately. The solution was stirred at ambient temperature for 3 h. The volume was reduced to about 10 mL by removal of methanol on a rotary evaporator, and ammonium hexafluorophosphate (141.8 mg. 0.87 mmol) was added. Then the solution was left in the freezer for 24 h; Dark colour powder was precipitated which was collected by filtration, washed with cold ethanol and diethyl ether, then finally dried in vacuum. Yield: 122.7 mg (86.7%). Anal. ESI-MS Calcd for $C_{23}H_{28}IN_4Os$: m/z 679.1. found 679.0. $^1$H NMR ((CD$_3$)$_2$CO) δ 9.43 (d, 1H, J=6 Hz), 8.65 (d, 1H, J=8 Hz), 8.29-8.22 (m, 3H), 7.64 (m, 1H), 6.97 (d, 2H, J=9 Hz), 6.59 (d, 1H, J=6 Hz), 6.30 (m, 3H), 3.41 (s, 3H), 2.80 (s, 6H), 2.63-2.56 (m, 1H), 1.00 (d of d, 6H). CHN analysis Found: C, 33.42%; H, 3.28%; N, 6.72%, Calcd for $C_{23}H_{28}F_6IN_4OsP$: C, 33.58% H, 3.43% N, 6.81%.

[($\eta^6$-bip)Os(Azpy)Cl]PF$_6$ (7)

[($\eta^6$-bip)OsCl$_2$]$_2$ (100.7 mg, 0.121 mmol) in methanol (40 mL) and water (10 mL) was heated under reflux under nitrogen for 2 h. The solution was hot-filtered to remove black residue, then Azpy (55 mg, 0.3 mmol) in methanol (5 mL) was added drop-wise, the solution colour changed from orange to black immediately. The solution was stirred and left to cool down to room temperature for 1 h. The volume was reduced to about 10 mL by removal of methanol on a rotary evaporator and ammonium hexafluorophosphate (215.0 mg. 1.32 mmol) was added. The solution was left at 277 K overnight. A brown powder precipitated, which was filtered off, washed with diethyl ether, then dried in a desiccator overnight. Yield: 109.4 mg (77.9%). Anal. ESI-MS Calcd for $C_{23}H_{19}ClN_3Os$: m/z 564.09. found 564.0. $^1$H NMR ((CD$_3$)$_2$CO) δ 9.47 (d, 1H, J=6 Hz), 8.98 (d, 1H, J=8 Hz), 8.46 (t, 1H, J=6 Hz), 7.97 (d, 2H, J=8 Hz), 7.97 (t, 1H, J=8 Hz), 7.74 (t, 1H, J=8 Hz), 7.61 (m, 4H), 7.51 (m, 3H), 6.96 (d, 1H, J=6 Hz), 6.89 (d, 1H, J=6 Hz), 6.77 (t, 1H, J=6 Hz), 6.70 (t, 1H, J=6 Hz), 6.45 (t, 1H, J=6 Hz). CHN analysis Found: C, 39.56%; H, 2.90%; N, 6.48%, Calcd for $C_{23}H_{19}F_6ClN_3OsP$: C, 39.80%; H, 3.07%; N, 5.81%.

[($\eta^6$-p-cym)Os(Azpy)Cl]PF$_6$ (8)

[($\eta^6$-p-cym)OsCl$_2$]$_2$ (40.7 mg, 0.0515 mmol) was dissolved in methanol (20 mL). Azpy (21.1 mg, 0.116 mmol) in 5 mL of methanol was added drop-wise. The solution colour changed from yellow to brown gradually, it was stirred at ambient temperature for 1 h; The volume was reduced to about 10 ml by removal of methanol on a rotary evaporator. Ammonium hexafluorophosphate (52.2 mg. 0.32 mmol) was added. Then the solution was left in the freezer for 24 h; Dark colour powder precipitated out, which was filtered off, washed with cold ethanol and diethyl ether, then finally dried in vacuum. Yield: 60.5 mg (85.4%). Anal. ESI-MS Calcd for $C_{21}H_{23}ClN_3Os$: m/z 544.1. found 544.1. $^1$H NMR ((CD$_3$)$_2$CO) δ 9.65 (d, 1H, J=6 Hz), 9.01 (d, 1H, J=9 Hz), 8.50-8.48 (m, 1H), 8.16 (d, 2H, J=8 Hz), 8.02-7.99 (m, 1H), 7.78 (m, 3H), 6.79 (d, 1H, J=6 Hz), 6.39 (d, 1H, J=6 Hz), 6.32 (m, 2H), 2.54 (m, 1H), 2.43 (s, 3H), 0.98 (d of d, 6H). CHN analysis Found: C, 36.61%; H, 3.21%; N, 6.10%, Calcd for $C_{21}H_{23}F_6ClN_3OsP$: C, 36.66%; H, 3.37%; N, 6.61%. Single crystals suitable for X-ray diffraction were obtained by slow evaporation of a methanol solution of complex 8 at ambient temperature.

[($\eta^6$-bip)Os(azpy-OH)Cl]PF$_6$ (9)

[($\eta^6$-bip)OsCl$_2$]$_2$ (51 mg, 0.061 mmol) in methanol (40 mL) and water (10 mL) was heated under reflux under nitrogen for 2 h. Azpy-OH (30.1 mg, 0.15 mmol) in methanol (2 mL) was added, the solution turned from orange to deep brown-red. Then the solution was hot-filtered and left to cool down to ambient temperature while stirring for 1 h. The volume was reduced to about 10 mL by removal of methanol on a rotary evaporator. Ammonium hexafluorophosphate (100.6 mg. 1.11 mmol) was added. The solution was left at 277 K for 0.5 h. A brown solid precipitated, which was collected by filtration, washed with diethyl ether and dried overnight in a desiccator. Yield: 42.0 mg (47.9%). Anal. ESI-MS Calcd for $C_{23}H_{19}ClN_3Os$: m/z 580.08. found 580.0. $^1$H NMR ((CD$_3$)$_2$CO) δ 9.37 (d, 1H, J=9 Hz), 8.83 (d, 1H, J=8 Hz), 8.39-8.34 (m, 1H), 8.01 (d, 2H, J=9 Hz), 7.80-7.50 (m, 1H), 7.61-7.59 (m, 2H), 7.50 (m, 3H), 7.02 (d, 2H, J=6 Hz), 6.86 (d, 1H, J=6 Hz), 6.76 (d, 1H, J=6 Hz), 6.72 (m, 2H), 6.45 (t, 1H). CHN analysis Found: C, 38.15%; H, 3.04%; N, 5.19%, Calcd for $C_{23}H_{19}F_6ClN_3OOsP$: C, 38.15%; H, 2.64%; N, 5.80%.

[($\eta^6$-p-cym)Os(Azpy-OH)Cl]PF$_6$ (10)

[($\eta^6$-p-cym)OsCl$_2$]$_2$ (50.1 mg, 0.063 mmol) was dissolved in methanol (50 mL). Azpy-OH (32.8 mg, 0.16 mmol) in methanol (10 mL) was added drop-wise. The solution was stirred at ambient temperature for 24 h with 4 drops of 1M HCl. The complex was purified by chromatography on a Sephadex LH20 column. Ammonium hexafluorophosphate (54.3 mg. 0.33 mmol) was added. The solvent was removed on a rotary evaporator. A brown solid was collected by filtration and washed with cold ethanol and diethyl ether, then finally dried under vacuum. Yield: 16.5 mg (18.6%). Anal. ESI-MS Calcd for $C_{21}H_{23}ClN_3OOs$: m/z 560.1. found 560.1. $^1$H NMR ((CD$_3$)$_2$CO) δ 9.58 (d, 1H, J=6 Hz), 9.93 (d, 1H, J=8 Hz), 8.39 (t, 1H, J=8 Hz), 8.19 (d, 2H, J=9 Hz), 7.82 (t, 1H, J=6 Hz), 7.15 (d, 2H, J=9 Hz), 6.72 (d, 1H, J=6 Hz), 6.43 (m, 2H), 6.34 (d, 1H, J=6 Hz), 3.35 (s, 3H), 2.63 (m, 1H), 1.00 (d of d, 6H). CHN analysis Found: C, 35.13%; H, 3.40%; N, 4.84%, Calcd for $C_{21}H_{23}F_6ClN_3OsP$: C, 35.82%; H, 3.29%; N, 5.97%.

[($\eta^6$-bip)Os(azpy-NMe$_2$)Cl]PF$_6$ (11)

[($\eta^6$-bip)OsCl$_2$]$_2$ (104 mg, 0.12 mmol) was dissolved in methanol (40 mL) and water (10 mL), the solution was heated to refluxed under nitrogen for 2 h at 248 K. Then Azpy-NMe$_2$ (70.626 mg, 0.3121 mmol) in 5 mL of methanol was added drop-wise. The solution turned from orange to purple, it was hot-filtered and left to cool to ambient temperature while stirring for 1 h. Then the solvent was evaporated on a rotary evaporator and ammonium hexafluorophosphate (182.23 mg. 1.11 mmol) was added. The solution was left at 277 K overnight. A purple solid precipitated and filtered off, washed with diethyl ether and dried overnight in a desiccator. Yield: 135.5 mg (89%). Anal. ESI-MS Calcd for $C_{26}H_{24}ClN_4Os$: m/z 607.13. found 607.0. $^1$H NMR ((CD$_3$)$_2$CO) δ 9.16 (d, 1H, J=6 Hz), 8.51 (d, 1H, J=8 Hz), 8.23-8.20 (m, 1H), 8.14 (d, 2H, J=6 Hz), 7.69-7.47 (m, 6H), 6.94 (d, 1H, J=6 Hz), 6.87 (d, 2H, J=6 Hz), 6.77 (d, 1H, J=6 Hz), 6.68-6.63 (m, 2H), 6.44 (t, 1H, J=6 Hz), 3.40 (s, 6H). CHN analysis Found: C, 39.99%; H, 3.16%; N, 7.45%, Calcd for $C_{25}H_{24}F_6ClN_4OsP$: C, 39.98%; H, 3.22%; N, 7.46%. Single crystals suitable for X-ray diffraction were obtained diffusion of diethyl ether into a solution of complex 11 in methanol at 277 K.

[($\eta^6$-p-cym)Os(Azpy-NMe$_2$)Cl]PF$_6$ (12)

[($\eta^6$-p-cym)OsCl$_2$]$_2$ (100.0 mg, 0.126 mmol) is dissolved in methanol (40 mL). Azpy-NMe$_2$ (57.4 mg, 0.254 mmol) in methanol (5 mL) was added drop-wise. The solution-colour changed from yellow to blue immediately, it was stirred at ambient temperature for 1 h. The volume was reduced to about 10 mL by removal of methanol on a rotary evaporator. Ammonium hexafluorophosphate (205.8 mg. 1.26 mmol) was added. Then the solution was left in the freezer for 24 h; A dark colour powder precipitated, which was collected by filtration and washed with cold ethanol and diethyl ether, then finally dried in vacuum. Yield: 148.5 mg (80.6%). Anal. ESI-MS Calcd for $C_{23}H_{28}ClN_4Os$: m/z 587.2. found 587.4. $^1$H NMR ((CD$_3$)$_2$CO) δ 9.04 (d, 1H, J=6 Hz), 8.58 (d, 1H, J=8 Hz), 8.31-8.23 (m, 3H), 7.70 (m, 3H), 6.58 (d, 1H, J=6 Hz), 6.32-6.26 (m, 3H), 2.80 (s, 6H), 2.48-2.45 (m, 1H), 2.47 (s, 3H), 0.96 (d of d, 6H). CHN analysis Found: C, 37.72%; H, 3.72%; N, 7.69%, Calcd for $C_{23}H_{28}F_6ClN_4OsP$: C, 37.78%; H, 3.86%; N, 7.66%.

[($\eta^6$-p-cym)Os(pp-NMe$_2$)I]PF$_6$ (13).

[($\eta^6$-p-cym)OsI$_2$]$_2$ (50.0 mg, 0.043 mmol) was dissolved in methanol (30 mL) at 313 K. pp-NMe$_2$ (19.5 mg, 0.086 mmol) in methanol (10 mL) was added drop-wise, the solution-colour changed from orange to red immediately. The solution was stirred at ambient temperature for 2 h. The volume was reduced to about mL by removal of methanol on a rotary evaporator, and ammonium hexafluorophosphate (141.8 mg. 0.87 mmol) was added. Then the solution was left in the freezer for 24 h. Dark coloured powder was precipitated which was collected by filtration, washed with cold ethanol and diethyl ether, then finally dried in vacuum. Yield: 50.7 mg (72.9%). ESI-MS Calcd for $C_{24}H_{28}IN_3Os$: m/z 821.6. found 821.6. $^1$H NMR ((CD$_3$)$_2$CO): δ 9.55 (d, 1H, J=5 Hz), 9.12 (s, 1H), 8.45 (d, 1H, J=7 Hz), 8.24 (t, 1H, J=7 Hz), 7.83 (d, 2H, J=9 Hz), 7.73 (t, 1H, J=5 Hz), 6.89 (d, 2H, J=9 Hz), 6.38 (d, 1H, J=6 Hz), 6.04 (d, 1H, J=6 Hz), 5.92-5.87 (m, 2H), 3.15 (s, 6H), 2.65 (s, 3H), 2.21-2.23 (m, 1H), 1.08 (d of d, 6H). CHN analysis. Found: C, 34.53%; H, 3.36%; N, 5.06%. Calcd for $C_{24}H_{28}F_6IN_3OsP$: C, 35.08% H, 3.56% N, 5.11%.

[($\eta^6$-bip)Os(pp)I]PF$_6$. (14)

This complex was prepared in an analogous manner to compound [($\eta^6$-p-cym)Os(pp-NMe$_2$)I]PF$_6$ from [($\eta^6$-bip)OsI$_2$]$_2$. Yield: 78.1%. Anal. Calcd. for $C_{24}H_{20}F_6IN_2OsP$: C, 36.10; H, 2.52; N, 3.51. Found: C, 34.91; H, 2.41; N, 3.34.

[($\eta^6$-p-cym)Os(pp)Cl]PF$_6$ (15).

This complex was prepared in an analogous manner to compound [($\eta^6$-p-cym)Os(pp-NMe$_2$)I]PF$_6$ from [($\eta^6$-p-cym)OsCl$_2$]$_2$. Yield: 77.4%. Anal. Calcd. for $C_{22}H_{24}ClF_6N_2OsP$: C, 38.46; H, 3.52; N, 4.08. Found: C, 38.44; H, 3.38; N, 4.06.

[($\eta^6$-p-cym)Os(pp-NMe$_2$)I]PF$_6$ (16).

This complex was prepared in an analogous manner to compound [($\eta^6$-p-cym)Os(pp-NMe$_2$)I]PF$_6$ from [($\eta^6$-p-cym)OsI$_2$]$_2$. Yield: 85.6%. Anal. Calcd. for $C_{24}H_{29}ClF_6N_3OsP$: C, 39.48; H, 4.00; N, 5.75. Found: C, 39.43; H, 3.89; N, 5.75.

Instrumentation.

NMR Spectroscopy.

$^1$H NMR spectra were acquired in 5 mm NMR tubes at 298 on either a Bruker DPX-400, Bruker DRX-500 or Bruker AV II 700. $^1$H NMR chemical shifts were referenced to acetone-d$_6$ (2.09 ppm). All data processing was carried out using MestReC or TOPSPIN version 2.0 (Bruker U.K. Ltd.).

Electrospray Ionisation Mass Spectrometry (ESI-MS).

Spectra were obtained by preparing the samples in 50% CH$_3$CN and 50% H$_2$O (v/v) and infusing into the mass spectrometer (Varian 4000). The mass spectra were recorded with a scan range of m/z 500-1000 for positive ions.

Elemental Analysis.

Elemental analysis (Carbon, hydrogen, and nitrogen) were carried out through Warwick Analytical Service using an Exeter analytical elemental analyzer (CE440).

UV-Vis Spectroscopy.

UV-vis spectra were recorded on a Cary 50-Bio spectrophotometer by using 1-cm path-length quartz cuvettes (0.5 mL) and a PTP1 Peltier temperature controller. Spectra were recorded at ca. 310 K in double distilled water from 800 to 200 nm.

Methods

N-Acetyl-L-Cysteine (NAC) Treatment.

A2780 cells were pre-treated with 5 mM NAC for 2 h to increase their GSH (glutathione) levels and then the complexes were added at concentrations above their IC$_{50}$ values: 2 (0.25 μM), 5 (0.25 μM), 12 (2.5 μM), 6 (0.25 μM) and cisplatin (5.0 μM) for another 24 h treatment. Then NAC and osmium complexes were removed at the same time and washed with PBS once, the cells were incubate for 72 h for recovery. The cell viability was tested by SRB test same as used for IC$_{50}$ test.

X-Ray Crystallography.

X-ray diffraction data for [(η⁶-p-cym)Os(Azpy)I]PF₆ (2), [(η⁶-bip)Os(Azpy-O)I].0.5H₂O (3*), [(η⁶-p-cym)Os(Azpy-NMe₂)I]PF₆ (5), [(η⁶-p-cym)Os(Azpy)I]PF₆ (8), [(η⁶-p-cym)Os(Azpy-NMe₂)Cl]PF₆ (11) and for [(η⁶-p-cym)OsI₂] I₂ were obtained on an Oxford Diffraction Gemini four-circle system with a Ruby CCD area detector using Mo K☐ radiation. Absorption corrections were applied using ABSPACK.[10] The crystals were mounted in oil and held at 100(2) K with the Oxford Cryosystem Cryostream Cobra. The structures were solved by direct methods using SHELXS (TREF)[11] with additional light atoms found by Fourier methods. Refinement used SHELXL 97.[12] H atoms were placed at geometrically calculated positions and refined riding on their parent atoms. The solvent water in 3* was refined as disordered over the inversion centre at 50% occupancy. Hydrogens were located in a difference map and allowed to refine freely but given thermal parameters equal to 1.5 time the equivalent isotropic value of the oxygen to which they are attached. The water forms short hydrogen bonds bridging the phenoxides of two neighbouring complexes (FIG. 1).

pH* Measurements.

The pH* (pH meter reading without correction for effects of deuterium on glass electrode) values of phosphate buffer was measured at ambient temperature. Before NMR spectra were recorded, using a corning 240 pH meter equipped with a microcombination electrode calibrated with Aldrich buffer solutions at pH 4, 7 and 10.

Determination of IC₅₀ Values.

SRB Growth Inhibition Assay

The concentrations of the osmium complexes that inhibit 50% of the proliferation of human ovarian A2780 cancer cells were determined by sulforhodamine B test. A2780 cells were seeded in 96-well plate (Falcon) at 5000 cells/well, after the incubation for 48 h, The complexes were solubilised in DMSO (Sigma) to provide 10 mM stocks. The stocks were serially diluted by cell culture media to give concentrations four-fold than the final concentrations for the assay. The dilutions of complexes in cell culture media were added to the 96-well plate with cells in triplicates to achieve the final concentrations. The final DMSO concentration in each well was no more than 1% (v/v). The complexes were removed after 24 h. The cells were washed with Phosphate Buffered Saline once and cell culture media was added 150 μL/well. The cells were recovered for 72 h. The surviving cells were fixed by adding 150 μL/well of 50% (w/v) trichloroacetic acid and incubated for 1 h at 277 K (277 K). The plates were washed with tap water three times and dried under a flow of warm air, 0.4% sulforhodamine B (Sigma) solution 100 μL/well followed by washing with 1% acetic acid five times and dried under a flow of warm air. The dye was dissolved in 10 mM Tris buffer 200 The absorbance of each well was obtained by the Multiskan Ascent plate reader (Labsystems) at 540 nm. The absorbance value of SRB in each well is directly proportional to the cell number. Then the absorbance can be plotted against concentration and the IC₅₀ determined by using Origin software.

MTT Growth Inhibition Assay.

Tumor cell growth inhibition was assessed using the MTT assay.[13] 2×10³ cells were inoculated into a 96-well plate and incubated overnight at 37° C. in a humidified atmosphere containing 5% CO₂. Complexes were solubilised in DMSO as above, and then diluted in complete cell culture medium to give a broad range of concentrations. Cisplatin was included in the screen as a comparator. Medium was removed from each well and replaced with complex or control solutions, and the plates then incubated for a further 96 hours. After 96 h culture medium was removed and 200 μL of 0.5 mg mL⁻¹ MTT solution (Sigma) in complete medium added to each well. Following further 4 h incubation, the solution was removed from each well and 150 μL of DMSO (Sigma) added to solubilise the formazan crystals resulting from MTT conversion. Absorbance values for the resulting solutions were read at 550 nm on a microplate reader and cell survival calculated as the absorbance of treated cells divided by the control. Results were expressed in terms of IC₅₀ values (i.e. concentration of compound required to kill 50% of cells) and all experiments were performed in triplicate.

Cell Lines.

The following human cancer cell lines were cultured in RPMI 1640 cell culture medium supplemented with 1 mM sodium pyruvate, 2 mM L-glutamine and 10% fetal bovine serum (all from Sigma): A549 non-small cell lung, HCT-116 colon, MCF-7 breast, PC-3 prostate (all from LGC Promochem, Teddington, UK), A2780/cis ovarian (cisplatin-resistant) and RT-112 bladder (both from ECACC, Salisbury, UK).

Animals.

Female Balb/c immunodeficient nude mice (Harlan, Loughborough, UK) aged 6-12 weeks were used. Mice received Harlan 2018 diet (Harlan) and water ad libitum. Mice were kept in cages in an air-conditioned room with regular alternating cycles of light and darkness. All animal procedures were carried out under a project license issued by the UK Home Office and UKCCCR guidelines (Workman P, Twentyman P, Balkwill F et al: United Kingdom Co-ordinating Committee on Cancer Research (UKCCCR) Guidelines for the Welfare of Animals in Experimental Neoplasia (Second Edition). Br J Cancer 77: 1-10, 1998) were followed throughout.

Evaluation of In Vivo Toxicity.

HCT-116 was used in the study. Tumours were excised from a donor animal, placed in sterile physiological saline containing antibiotics and cut into small fragments of approximately 2 mm³. Under brief general inhalation anaesthesia, fragments were implanted in the left right abdominal flank of each mouse using a trocar. Once the tumours could accurately be measured using callipers (mean tumour volume of approximately 50 mm³), treatment commenced. Complexes 3 and 6 were solubilised in 10% DMSO; 5% Tween-80; 85% saline and were administered intravenously to groups of 2 mice on day 0. Animals were weighed frequently and monitored for any deleterious effects over a period of 15 days. Increasing doses of complexes starting at 2 mg kg⁻¹ were administered with no evident toxicity until a maximum soluble dose of 40 mg kg⁻¹ was achieved.

GSH Reaction.

A solution containing [(η⁶-p-cym)Os(Azpy-NMe₂)I]PF₆ (6) (100 μM) and GSH (10 mM) was incubated at 310 K in 95% phosphate buffer (10 mM) and 5% methanol and was monitored by ¹H-NMR spectroscopy for a period of 24 h.

Results and Discussion

Previously we reported the synthesis of the two Os$^{II}$ azopyridine complexes [(η⁶-arene)Os(azpy-NMe₂)Cl]PF₆ with arene=biphenyl (11) and p-cymene (12).[14] Cytotoxicity tests for these complexes were hampered by their low solubility and the occurrence of precipitation under the test conditions used. No activity towards human A549 lung cancer cells was detected up to concentrations of 100 μM. In the present work we have explored complexes with iodide replacing chloride, with a dimethylamine or hydroxyl substituent on the phenyl ring of the phenylazopyridine chelating ligand, and also checked that the complexes remained in solution under the test conditions and did not precipitate (vide infra).

Chemistry.

Figure 1A:
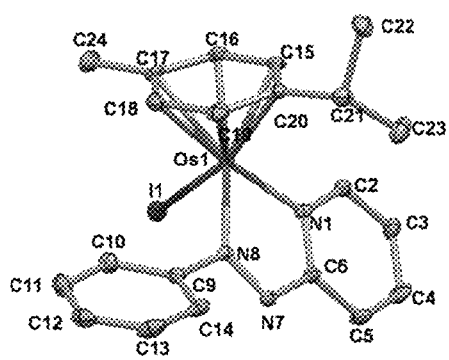
FIGS. 1A-1E show the X-ray structures of compounds according to the present invention.
Figure 1B:
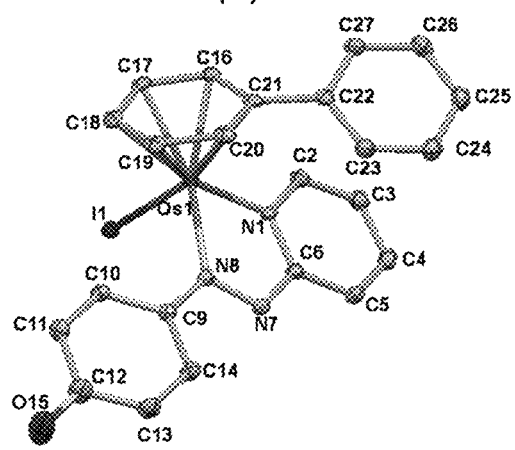
Figure 1C:
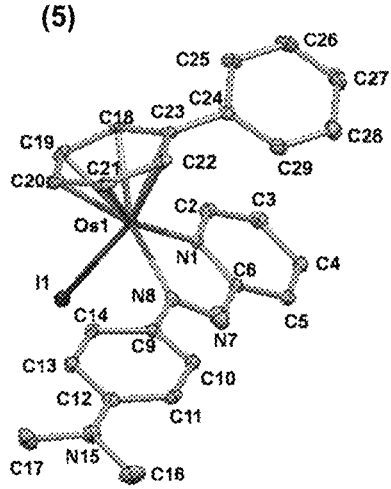
Figure 1D:
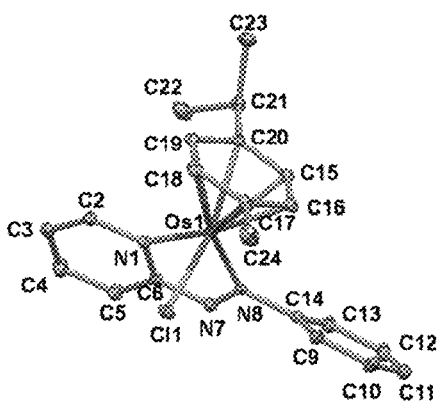
Figure 1E:
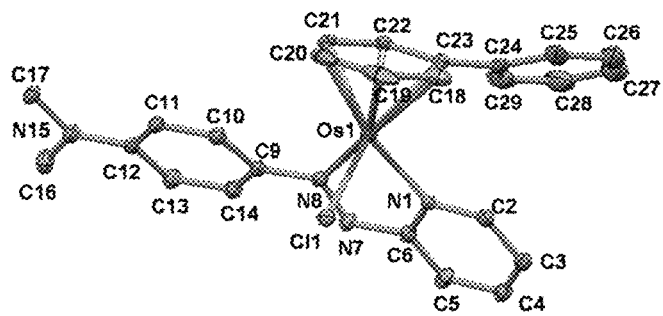
Figure 2:
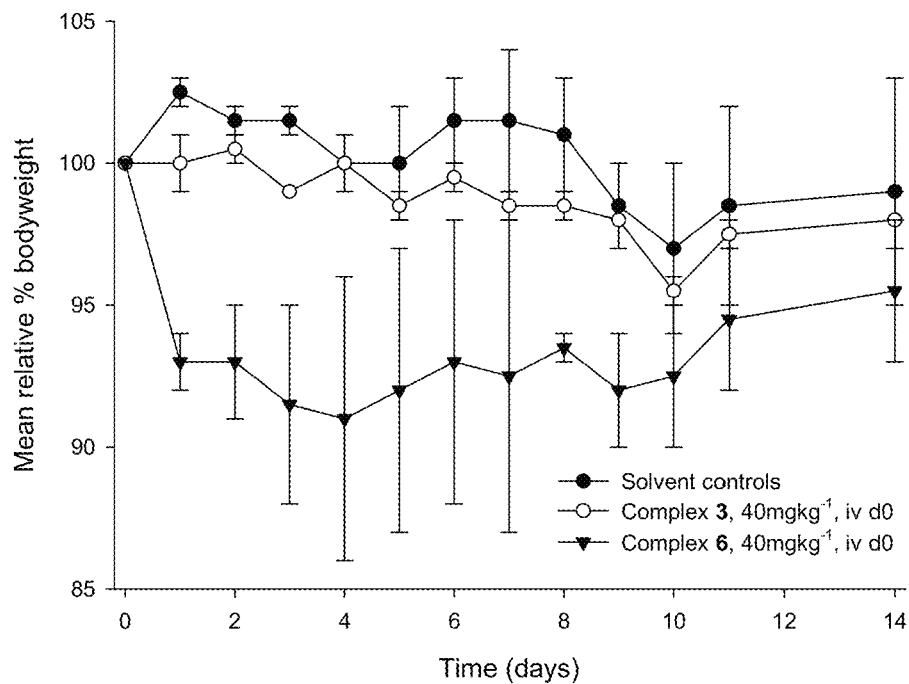
FIG. 2 shows the results of mean body weight experiments of mice bearing human tumour xenografts following administration of compounds according to the present invention.
Figure 3:
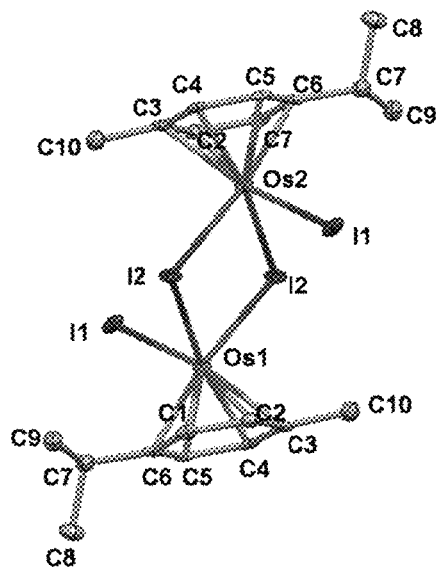
FIG. 3 shows the X-ray structure of $[(\eta^6\text{-p-cym})OsI_2]_2$.
Figure 5B:
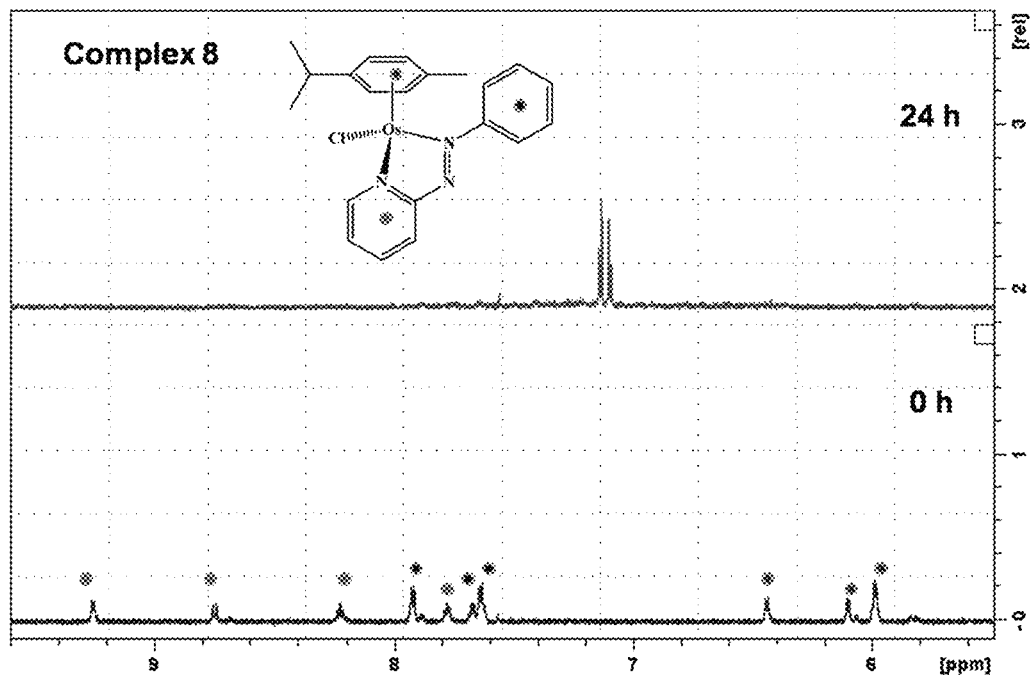
Figure 5C:
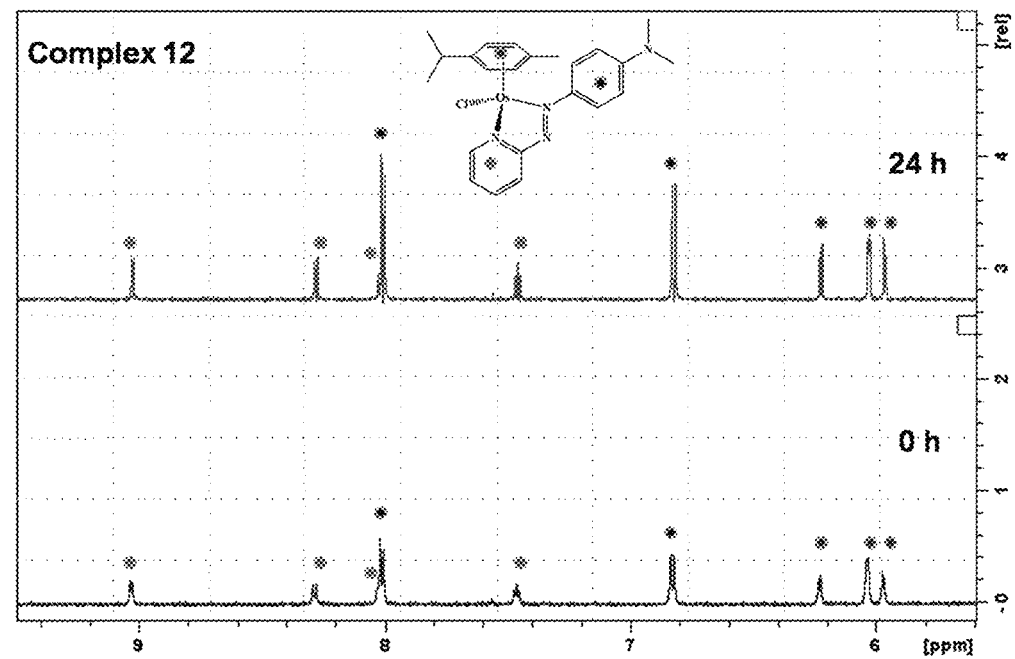
Figure 6:
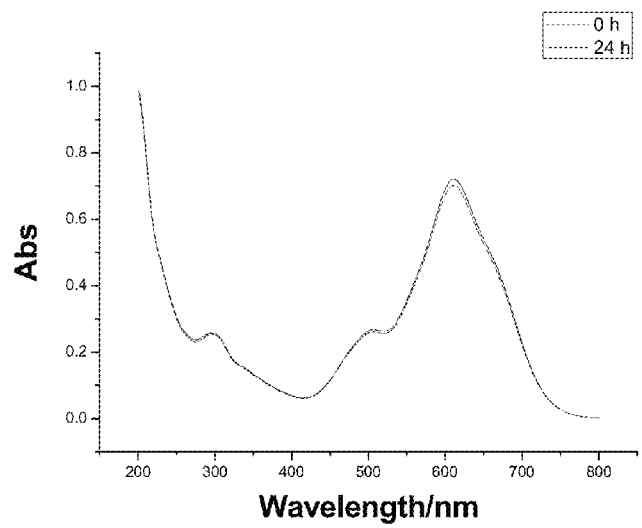
Figure 7:
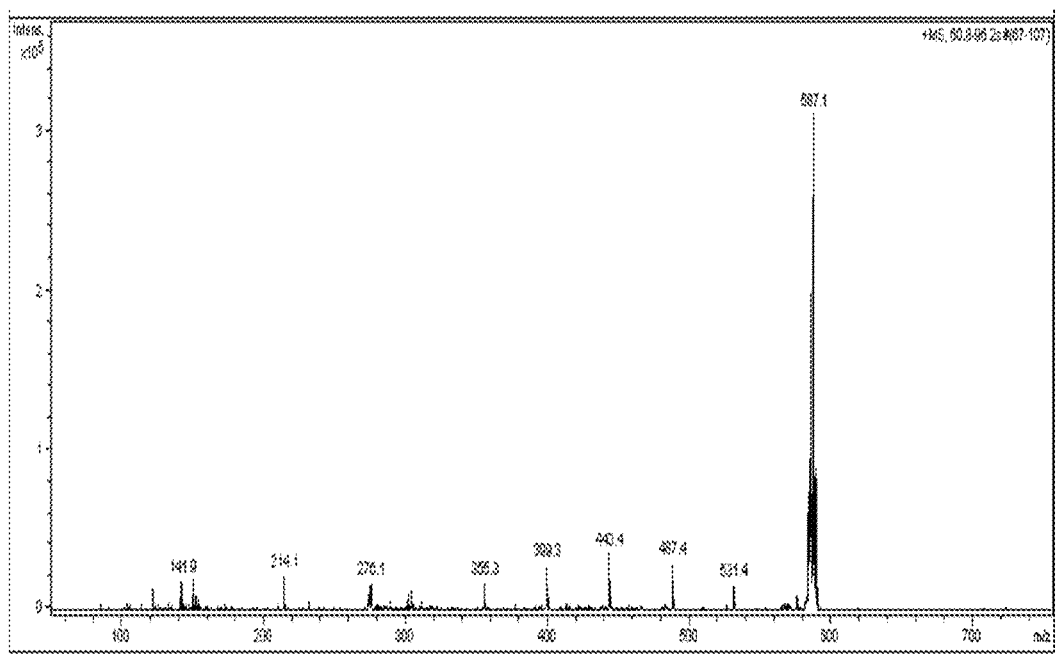

Six novel iodido osmium arene complexes containing chelated phenylazopyridine ligands (Azpy, Azpy-OH and Azpy-NMe$_2$) were synthesized in good yields with PF$_6$ as the counter anion. In general they have poor aqueous solubility, with the biphenyl complexes being less water-soluble than the para-cymene complexes. The structures of the iodido Azpy complex 2, the Azpy-OH complex 3 and the Azpy-NMe$_2$ 5 were determined by X-ray crystallography. For comparison, six chlorido analogues were synthesized and the structures of the Azpy complex 8 and Azpy-NMe$_2$ complex 11 were also determined by X-ray crystallography. We have reported the X-ray structure of 12 previously.[14] We also determined the structure of the dimer [($\eta^6$-p-cym)OsI$_2$]$_2$ which is an important synthetic intermediate in this work (FIG. 3).

All the osmium complexes adopt the familiar pseudo-octahedral 'piano-stool' structure in the crystalline state, (FIG. 1) with bond lengths and angles within the expected ranges. The crystal [($\eta^6$-bip)Os(azpy-O)I].0.5H$_2$O (3) obtained by slow evaporation of a methanolic solution of complex 3 [($\eta^6$-bip)Os(Azpy-OH)I]PF$_6$ has no counter ion and a short O15-C12 bond length (1.258(4) Å) indicating deprotonation of the OH group, with iodide balancing the change on Os$^{II}$. A water molecule in the lattice forms a short H-bond with the phenoxide group and bridges two phenoxides of neighbouring complexes, This provides a rare example of a structure in this class for a deprotonated osmium arene complex without a counter-ion (FIG. 4). The pK$_a$ of the hydroxyl group of 3 was determined to be less than 7 (comparable with a value of 6.48 for the ruthenium analogue)[15] and so the complex would be expected to be deprotonated under the conditions of the cytotoxicity assays (pH 7), as in the X-ray structure. Selected bond lengths and angles for these structures are listed in the supporting information (Table 2).

Cytotoxicity.

Under the conditions used here, and in contrast to previous studies on complexes 11 and 12,[14] the complexes appeared to be soluble in the culture medium at the concentrations tested and no precipitation was observed after 24 h. None of the azopyridine ligands themselves showed any anti-proliferative activity against A2780 human ovarian cancer cells line at concentrations up to 100 µM. The IC$_{50}$ values of the osmium complexes with phenyl azopyridine derivatives as the chelating ligand ranged from 0.14 µM for the iodido biphenyl complexes 3 and 5 with Azpy-OH and Azpy-NMe$_2$ ligands, to more than 50 µM for the chlorido complex 8 containing Azpy.

The IC$_{50}$ values for complexes 1-12 against the A2780 human ovarian cancer cell line are given in Table 1A. The IC$_{50}$ values for complexes 13-16 against A2780 human ovarian cancer cell line are given in Table 1B From the preliminary results against the A2780 cell line, 3 complexes were selected for further evaluation against cancer cell lines of differing histotype, and also against a cisplatin-resistant subline of A2780, A2780/cis. As can be seen from Table 10, complexes 3 and 6 demonstrated at least 10-fold greater potency than cisplatin against all cell lines tested apart from RT-112 which demonstrated a 3-fold difference for complex 3. Complex 12 demonstrated similar potency to cisplatin over the panel. The biggest differential for all 3 complexes was seen for the PC-3 cell line.

Evaluation of In Vivo Toxicity.

Complex 3 and 6 were selected for further evaluation in vivo based on their promising in vitro activity. On evaluation of their toxicity in a nude mouse tumour HCT-116 xenograft model, the complexes demonstrated negligible deleterious effects at doses up to and including their maximum soluble dose of 40 mg kg$^{-1}$. This dose is approximately 6 times higher than the maximum tolerated dose of cisplatin in the same tumour model, and suggests that with the comparative lack of toxicity of the complexes there is likely to be a much broader therapeutic window. This will be investigated in extensive in vivo pharmacokinetic and efficacy studies.

Stability and Hydrolysis.

We investigated the hydrolysis (aquation) of these azopyridine complexes since this is a potential mechanism for activation of halido osmium arene complexes in their reactions with biological targets such as DNA.[6]

The aqueous behavior of the highly active complexes 6, moderately active complex 12, and inactive complex 8 was studied at 310 K over 24 h. As judged by the observation of their $^1$H NMR spectra in 95% deuterated phosphate buffer (10 mM)/5% MeOD-d$_4$, which remained unchanged, (FIG. 5) mass spectra, which showed ions corresponding to the chlorido and iodido complexes, and UV-vis spectra, (FIG. 6) which also showed no change, complexes 6 and 12 remained stable and did not hydrolyze over a period of 24 h.

In contrast, the $^1$H NMR spectrum of a 50 µM solution of complex 8 in 95% 10 mM D$_2$O phosphate buffer/5% MeOD-d$_4$ showed the disappearance of the peaks corresponding to the azopyridine ligand suggesting that the complex is less stable that the iodido complexes. An attempt to remove the chloride from complex 12 by reacting it with silver nitrate under reflux overnight, did not lead to an aqua product, only the chlorido complex was shown in the mass spectra (FIG. 7), indicating that the Os—Cl bond is strong. We therefore concluded that the most active complexes are stable and relatively inert towards hydrolysis.

Effect of N-Acetyl-L-Cysteine on Cytotoxicity

Pretreatment of cells with NAC can block cisplatin-dependent caspase-3 activation and apoptosis by inhibiting the accumulation of intracellular reactive oxygen species (ROS) and maintaining intracellular GSH levels.[16] In order to investigate possible involvement of ROS in the cytotoxicity of phenylazopyridine Os$^{II}$ arene complexes, we therefore investigated the effect of pretreatment of the cells with NAC. Cisplatin was used as the positive control, whereas cells not treated with osmium complexes served as the negative control.

A2780 cells were treated with concentrations of the iodido complexes 3, 5 and 6 and the chlorido complex 12 which were 1.2-1.8× higher than their IC$_{50}$ values and 2.5× in the case of cisplatin. These doses reduced cell growth to <30% of the control value (FIG. 8). When the cells were pretreated with 5 mM N-acetyl-L-cysteine for 2 h to increase the intracellular glutathione concentration,[15] the antiproliferation effects of all the complexes were markedly inhibited. Growth levels of >70% were restored. The exception was the chlorido complex 12, for which NAC pretreatment had only a small effect on restoring growth (FIG. 8). The suggests that, unlike these azopyridine osmium arene iodido complexes or cisplatin, the chlorido complexes do not depend on the production of ROS for their mechanism of cytotoxicity.

Since it was possible that the complexes might react directly with NAC and that the effects are not merely due to effects on thiol levels in cells, the $^1$H NMR spectrum of a solution containing 1.0 mM [($\eta^6$-p-cym)Os(Azpy-NMe$_2$)I]

PF$_6$ (6) and excess (7.35 mM) NAC in 30% acetone-d$_6$ and 70% phosphate buffer (10 mM pH=7.0) was monitored for a period of 24 h at 310 K. No new peaks appeared in the NMR spectrum (FIG. 9) suggesting that this iodido osmium azopyridine complex does not readily react with NAC.

Reaction with GSH.

Since some phenylazopyridine ruthenium arene complexes appear to oxidize GSH catalytically, similar reactions were studied for the osmium analogues. The $^1$H NMR spectrum of a solution containing the highly cytotoxic iodido complex [(η$^6$-p-cym)Os(Azpy-NMe$_2$)I]PF$_6$ (6) (100 µM) and a 100× molar excess of GSH (10 mM, to mimic possible intracellular conditions) showed little change over a period of 24 h. This suggests that complex 6 does not catalytically oxidize GSH, unlike the behavior of the analogous Ru$^{II}$ complex which catalytically oxidizes GSH to GSSG,[15] The mechanism of cytotoxicity of these Os$^{II}$ azopyridine complexes therefore appears to differ from that of the Ru$^{II}$ analogues, perhaps explaining why the Os$^{II}$ complexes are more potent.

Conclusion

Organometallic osmium arene complexes have potential for exploration as anticancer complexes. Their rates of ligand substitution and their redox properties (metal- or ligand-centered) are controlled by the choice of the ligands. Pseudo-octahedral 'piano-stool' arene complexes are attractive since they provide an hydrophobic arene face amenable to a wide variety of substitutions together with 3 other variable coordination positions. Both the arene and the other ligands can have a major effect on determining the electron distribution within a complex. In the present case the chelated azopyridine ligand is both a σ-donor and a strong π-acceptor, ie. there is a strong back-donation of electrons from Os$^{II}$ onto the azopyridine ligand which has a large effect on reactivity. Iodido complexes were more active than chlorido complexes and those containing p-hydroxyl or p-dimethylamino substituents on the phenylazopyridine chelating ligand (e.g. complexes 3 and 6) were cytotoxic at nanomolar concentrations towards ovarian, lung, breast, colon, prostate, and bladder cancer cells, an order of magnitude more potent than cisplatin, and (unexpectedly) than their Ru$^{II}$ analogues. They are also inert to hydrolysis, but unlike their Ru$^{II}$ analogues do not oxidize GSH catalytically. Cytotoxicity was inhibited by pre-treatment of the cells with N-acetyl-L-cysteine suggesting that reactive oxygen species (ROS) are involved in their mechanism of action. These Os$^{II}$ complexes exhibited low toxicity and negligible deleterious effects in a HCT-116 tumour xenograft model which might provide them with a broad therapeutic window.

Further Complexes and Studies

The present inventors have synthesised further complexes and also carried out further studies, the details of which are shown below:

Ligand Names:

| | |
|---|---|
| 1-CF$_3$-4-Cl-Azpy | 2-Choro-5-trifluoromethyl-2-(phenylazo)pyridine |
| 1-Cl-Azpy | 5-Choro-2-(phenylazo)pyridine |
| 2-F-Azpy | 4-Fluoro-2-(phenylazo)pyridine |
| 2-Cl-Azpy | 4-Choro-2-(phenylazo)pyridine |
| 2-Br-Azpy | 4-Bromo-2-(phenylazo)pyridine |
| 2-I-Azpy | 4-Iodo-2-(phenylazo)pyridine |
| 3-Cl-Azpy | 3-Choro-2-(phenylazo)pyridine |
| OH-Azpy-NO$_2$ | 5-Hydroxyl-2-(4-nitrophenylazo)pyridine |
| Imine-S | N-(2-pyridylmethylene)-(S)-1-phenylethylamine |
| Imine-R | N-(2-pyridylmethylene)-(R)-1-phenylethylamine |

| Chemical Name | Structure | IC$_{50}$ to A2780 cell line/µM |
|---|---|---|
| [Os(η$^6$-bip)(pp-NMe$_2$)I]PF$_6$ FY012 | | 0.14(±0.01) |
| [Os(η$^6$-bip)(pp)Cl]PF$_6$ FY098 | | 4.6(±0.4) |

-continued

| Chemical Name | Structure | IC$_{50}$ to A2780 cell line/μM |
|---|---|---|
| [Os(η$^6$-bip)(pp-OH)Cl]PF$_6$ FY150 | | 2.4(±1.1) |
| [Os(η$^6$-p-cym)(pp-OH)Cl]PF$_6$ FY119 | | 5.5(±0.6) |
| [Os(η$^6$-bip)(pp-NMe$_2$)Cl]PF$_6$ FY093 | | 0.44(±0.01) |
| [Os(η$^6$-bip)(1-CF$_3$-4-Cl-Azpy)I]PF$_6$ FY107 | | 5.7(±1.0) |

-continued

| Chemical Name | Structure | IC$_{50}$ to A2780 cell line/μM |
|---|---|---|
| [Os(η$^6$-bip)(1-Cl-azpy)I]PF$_6$ FY110 | [PF$_6$] | 3.7(±0.3) |
| [Os(η$^6$-p-cym)(1-Cl-Azpy)I]PF$_6$ FY112 | [PF$_6$] | 9.0(±4.5) |
| [Os(η$^6$-bip)(2-F-Azpy)I]PF$_6$ FY069 | [PF$_6$] | 0.63(±0.1) |
| [Os(η$^6$-bip)(2-Cl-Azpy)I]PF$_6$ FY078 | [PF$_6$] | 1.0(±0.1) |

-continued

| Chemical Name | Structure | IC$_{50}$ to A2780 cell line/μM |
|---|---|---|
| [Os($\eta^6$-bip)(2-Br-Azpy)I]PF$_6$ FY061 | [PF$_6$]⁻ | 0.59(±0.02) |
| [Os($\eta^6$-bip)(2-I-Azpy)I]PF$_6$ FY070 | [PF$_6$]⁻ | 0.22(±0.02) |
| [Os($\eta^6$-p-cym)(2-I-Azpy)I]PF$_6$ FY067 | [PF$_6$]⁻ | 2.4(±0.5) |
| [Os($\eta^6$-bip)(3-Cl-Azpy)I]PF$_6$ FY052 | [PF$_6$]⁻ | 22.0(±2.0) |

-continued

| Chemical Name | Structure | IC$_{50}$ to A2780 cell line/μM |
|---|---|---|
| [Os(η$^6$-p-cym)(abpy))I]PF$_6$ FY043 | | 10.8(±0.11) |
| [Os(η$^6$-p-cym)(OH-Azpy-NO$_2$)I]PF$_6$ FY036 | | 0.29(±0.04) |
| [Os(η$^6$-p-cym)(OH-Azpy-NO$_2$)Cl]PF$_6$ FY033 | | 0.30(±0.05) |

| Chemical Name | Structure | IC$_{50}$ to A2780 cell line/μM |
|---|---|---|
| [(η$^6$-p-cym)Os(Imine-S)I]PF$_6$ FY175A | | 6.9 (±0.2) |
| [(η$^6$-p-cym)Os(Imine-R)I]PF$_6$ FY178A | | 0.30 (±0.02) |

The cytotoxicity studies were carried out as described previously above.

Synthesis and Characterization:

(FY012) [(η$^6$-bip)Os(pp-NMe$_2$)I]PF$_6$

[(η$^6$-bip)OsI$_2$]$_2$ (50.0 mg, 0.042 mmol) was dissolved in methanol (30 mL) at 353 K. pp-NMe$_2$ (18.8 mg, 0.84 mmol) in methanol (10 mL) was added drop-wise, the solution-colour changed from orange to red immediately. The solution was stirred at 353K for 4 h. The volume was reduced to about 10 mL by removal of methanol on a rotary evaporator, and ammonium hexafluorophosphate (27.3 mg. 0.17 mmol) was added. Then the solution was left in the freezer for 24 h. red colour powder was precipitated which was collected by filtration, washed with cold ethanol and diethyl ether, then finally dried in vacuum. Yield: 35.1 mg (49.8%). ESI-MS Calcd for C$_{26}$H$_{25}$IN$_3$Os: m/z 698.1. found 698.1. $^1$H NMR ((CD$_3$)$_2$CO): δ 9.29 (d, 1H, J=5 Hz), 9.02 (s, 1H), 8.42 (d, 1H, J=8 Hz), 8.18 (t, 1H, J=8 Hz), 7.65 (d, 2H, J=9 Hz), 7.51-7.38 (m, 7H). 6.88 (d, 1H, J=6 Hz), 6.74 (d, 2H, J=9 Hz), 6.62 (t, 1H, J=6 Hz), 6.55 (d, 1H, J=6 Hz), 6.50 (t, 1H, J=6 Hz), 6.34 (t, 1H, J=6 Hz), CHN analysis. Found: C, 41.54%; H, 3.31%; N, 5.61%. Calcd for C$_{24}$H$_{29}$ClF$_6$N$_3$OsP: C, 41.63% H, 3.36% N, 5.60%.

(FY098) [(η$^6$-bip)Os(pp)Cl]PF$_6$

[(η$^6$-bip)OsCl$_2$]$_2$ (50.0 mg, 0.060 mmol) was dissolved in methanol (30 mL) at 353 K. pp (21.9 mg, 0.12 mmol) in methanol (10 mL) was added drop-wise, the solution-colour changed from orange to red immediately. The solution was stirred at 353 K for 4 h. The volume was reduced to about 10 mL by removal of methanol on a rotary evaporator, and ammonium hexafluorophosphate (39.1 mg. 0.24 mmol) was added. Then the solution was left in the freezer for 24 h. Dark colour powder was precipitated which was collected by filtration, washed with cold ethanol and diethyl ether, then finally dried in vacuum. Yield: 64.0 mg (75.3%).ESI-MS Calcd for C$_{24}$H$_{20}$ClN$_2$Os: m/z 563.1. found 563.0.

$^1$H NMR ((CD$_3$)$_2$CO): δ 9.42 (d, 1H, J=5 Hz), 9.28 (s, 1H), 8.53 (d, 1H, J=8 Hz), 8.34 (t, 1H, J=8 Hz), 7.80 (t, 1H, J=8 Hz), 7.62 (d, 2H, J=9 Hz), 7.58 (d, 2H, J=9 Hz), 7.54-7.45 (m, 6H). 6.71 (d, 1H, J=6 Hz), 6.45 (d, 1H, J=6 Hz), 5.45-5.40 (m, 2H). 6.36 (t, 1H, J=6 Hz), CHN analysis. Found: C, 40.77%; H, 2.79%; N, 3.91%. Calcd for C$_{24}$H$_{20}$ClF$_6$N$_2$OsP: C, 40.77% H, 2.85% N, 3.96%.

(FY150) [(η$^6$-bip)Os(pp-OH)Cl]PF$_6$

[(η$^6$-bip)OsCl$_2$]$_2$ (50.0 mg, 0.060 mmol) was dissolved in methanol (20 mL) and water (10 mL) mixture at 353 K. pp-OH (23.8 mg, 0.012 mmol) in methanol (10 mL) was added drop-wise, The solution was stirred at 353 K for 4 h. The volume was reduced to about 10 mL by removal of methanol on a rotary evaporator, and ammonium hexafluorophosphate (97.8 mg. 0.6 mmol) was added. Then the solution was left in the freezer for 24 h. Dark colour powder was precipitated which was collected by filtration, washed with cold ethanol and diethyl ether, then finally dried in vacuum. Yield: 15.3 mg (17.2%). ESI-MS Calcd for C$_{24}$H$_{20}$ClN$_2$OOs: m/z 579.1. found 579.0. $^1$H NMR ((CD$_3$)$_2$CO): δ 9.36 (d, 1H, J=6 Hz), 9.18 (s, 1H), 8.47 (d, 1H, J=8 Hz), 8.29 (t, 1H, J=8 Hz), 7.76 (t, 1H, J=9 Hz), 7.58 (d, 2H, J=8 Hz), 7.54-7.43 (m, 5H), 6.92 (d, 2H, J=9 Hz), 6.74 (d, 1H, J=6 Hz), 6.64 (d, 1H, J=6 Hz), 6.45 (t, 1H, J=6 Hz), 6.42 (t, 1H, J=6 Hz), 6.35 (t, 1H, J=6 Hz), CHN analysis. Found: C, 39.44%; H, 2.84%; N, 3.71%. Calcd for C$_{24}$H$_{20}$ClF$_6$N$_2$OOsP: C, 39.87% H, 2.79% N, 3.87%.

(FY119) [(η$^6$-p-cym)Os(pp-OH)Cl]PF$_6$

[(η$^6$-p-cym)OsCl$_2$]$_2$ (50.0 mg, 0.063 mmol) was dissolved in methanol (30 mL) at 313 K. pp-OH (25.0 mg, 0.12 mmol) in methanol (10 mL) was added drop-wise, the solution-colour changed from orange to red immediately. The solution was stirred at ambient temperature for 2 h. The volume was reduced to about 10 mL by removal of methanol on a rotary evaporator, and ammonium hexafluorophosphate (41.2 mg. 0.25 mmol) was added. Then the solution was left in the freezer for 24 h. Dark colour powder was precipitated which was collected by filtration, washed with cold ethanol and diethyl ether, then finally dried in vacuum. Yield: 53.8 mg (63.7%). ESI-MS Calcd for C$_{22}$H$_{24}$ClN$_2$OOs: m/z 559.1. found 559.1. $^1$H NMR ((CD$_3$)$_2$CO): δ 9.60 (d, 1H, J=5 Hz), 9.35 (s, 1H), 8.50 (d, 1H, J=7 Hz), 8.34 (t, 1H, J=7 Hz), 7.84 (t, 1H, J=6 Hz), 7.75 (d, 2H, J=9 Hz), 7.08 (d, 2H, J=9 Hz), 6.46 (d, 1H, J=6 Hz), 6.00 (d, 1H, J=6 Hz), 5.84 (d, 1H, J=6 Hz), 2.81 (s, 3H), 2.65-2.55 (m, 1H), 2.41 (s, 6H), 1.09 (d of d, 6H). CHN analysis. Found: C, 37.82%; H, 3.33%; N, 3.91%. Calcd for C$_{22}$H$_{24}$ClF$_6$N$_2$OOsP: C, 37.58% H, 3.44% N, 3.98%.

(FY093) [(η$^6$-bip)Os(pp-NMe$_2$)Cl]PF$_6$

[(η$^6$-bip)OsCl$_2$]$_2$ (50.0 mg, 0.060 mmol) was dissolved in methanol (20 mL) at 313 K. pp-NMe$_2$ (27.1 mg, 0.12 mmol) in methanol (10 mL) was added drop-wise, the solution-colour changed from orange to red immediately. The solution was stirred at 353K for 12 h. The volume was reduced to about 10 mL by removal of methanol on a rotary evaporator, and ammonium hexafluorophosphate (39.1 mg. 0.24 mmol) was added. Then the solution was left in the freezer for 24 h. red colour powder was precipitated which was collected by filtration, washed with cold ethanol and diethyl ether, then finally dried in vacuum. Yield: 52.0 mg (57.8%). ESI-MS Calcd for C$_{24}$H$_{20}$ClN$_2$Os: m/z 563.1. found 563.0. $^1$H NMR ((CD$_3$)$_2$CO): δ 9.31 (d, 1H, J=5 Hz), 9.09 (s, 1H), 8.39 (d, 1H, J=8 Hz), 8.25 (t, 1H, J=8 Hz), 7.70 (t, 1H, J=9 Hz), 7.61-7.44 (m, 7H). 6.77 (d, 2H, J=9 Hz), 6.74 (d, 1H, J=6 Hz), 6.62 (d, 1H, J=6 Hz), 6.63-6.45 (m, 2H), 6.34 (t, 1H, J=6 Hz), CHN analysis. Found: C, 41.54%; H, 3.31%; N, 5.61%. Calcd for C$_{24}$H$_{20}$ClF$_6$N$_2$OsP: C, 41.63% H, 3.36% N, 5.60%.

(FY107) [Os(η$^6$-bip)(1-CF$_3$-4-Cl-azpy)I]PF$_6$.

[Os(η$^6$-bip)I$_2$]$_2$ (50.0 mg, 0.042 mmol) was dissolved in methanol (40 mL) at 353 K. 1-CF$_3$-4-Cl-azpy (24.0 mg, 0.084 mmol) in methanol (10 mL) was added drop-wise. The solution was stirred at 353 K for 16 h. The volume was reduced to about 10 mL by removal of methanol on a rotary evaporator, and ammonium hexafluorophosphate (27.7 mg. 0.17 mmol) was added. The solution was then left in the freezer for 24 h. Dark colored powder was precipitated which was collected by filtration, washed with cold ethanol and diethyl ether, then finally dried in vacuum. Yield: 43.1 mg (57.1%). ESI-MS Calcd for C$_{24}$H$_{17}$ClF$_3$IN$_3$Os: m/z 758.0. found 757.8. $^1$H NMR ((CD$_3$)$_2$CO): δ 9.80 (s, 1H), 8.71 (d, 1H, J=2 Hz), 7.96 (d, 2H, J=8 Hz), 7.72 (t, 1H, J=8 Hz), 7.56-7.44 (m, 6H), 7.42-7.38 (m, 2H), 7.27 (t, 1H, J=6 Hz), 7.22 (d, 1H, J=6 Hz), 6.98 (t, 1H, J=6 Hz), 6.88 (d, 1H, J=6 Hz), 6.77 (t, 1H, J=6 Hz), CHN analysis. Found: C, 31.98%; H, 2.08%; N, 4.34%. Calcd for C$_{24}$H$_{17}$ClF$_9$IN$_3$OsP: C, 31.96% H, 1.90% N, 4.66%.

(FY110) [Os(η$^6$-bip)(1-Cl-azpy)I]PF$_6$.

[Os(η$^6$-bip)I$_2$]$_2$ (30.0 mg, 0.025 mmol) was dissolved in methanol (40 mL) at 353 K. 1-Cl-azpy (10.8 mg, 0.050 mmol) in methanol (10 mL) was added drop-wise. The solution was stirred at 353 K for 2 h. The volume was reduced to about 10 mL by removal of methanol on a rotary evaporator, and ammonium hexafluorophosphate (16.3 mg. 0.10 mmol) was added. The solution was then left in the freezer (253K) for 24 h. Dark colored powder was precipitated which was collected by filtration, washed with cold ethanol and diethyl ether, then finally dried in vacuum. Yield: 22.0 mg (52.8%). ESI-MS Calcd for C$_{23}$H$_{15}$ClIN$_3$Os: m/z 690.0. found 689.9. $^1$H NMR ((CD$_3$)$_2$CO): δ 8.56 (d, 1H, J=6 Hz), 8.33 (t, 1H, J=8 Hz), 8.19 (d, 1H, J=6 Hz), 7.87 (d, 2H, J=8 Hz), 7.66 (t, 1H, J=8 Hz), 7.52-7.39 (m, 7H), 7.19 (d, 1H, J=6 Hz), 7.00 (t, 2H, J=6 Hz), 6.99-6.78 (m, 2H). CHN analysis. Found: C, 32.82%; H, 2.08%; N, 4.75%. Calcd for C$_{23}$H$_{15}$ClF$_6$IN$_3$OsP: C, 33.12%; H, 2.18%; N, 5.04%.

(FY112) [Os(η$^6$-p-cym)(1-Cl-azpy)I]PF$_6$.

[Os(η$^6$-p-cym)I$_2$]$_2$ (50.0 mg, 0.043 mmol) was dissolved in methanol (30 mL). 1-Cl-azpy (18.7 mg, 0.086 mmol) in methanol (10 mL) was added drop-wise. The solution was stirred at 353 K for 4 h. The volume was reduced to about 10 mL by removal of methanol on a rotary evaporator, and ammonium hexafluorophosphate (28.0 mg. 0.17 mmol) was added. The solution was then left in the freezer (253K) for 24 h. Dark colored powder was precipitated which was collected by filtration, washed with cold ethanol and diethyl ether, then finally dried in vacuum. Yield: 28.0 mg (40.0%). ESI-MS Calcd for C$_{21}$H$_{22}$ClIN$_3$Os: m/z 670.0. found 669.9. $^1$H NMR ((CD$_3$)$_2$CO): δ 9.01 (d, 1H, J=6 Hz), 8.20 (d, 1H, J=8 Hz), 8.14-8.02 (m, 3H), 7.81 (m, 1H), 7.14 (d, 2H, J=9 Hz), 6.61 (m, 2H), 6.46 (d, 1H, J=6 Hz), 6.16 (m, 4H), 2.39 (s, 3H), 2.69-2.64 (m, 1H), 1.03 (d of d, 6H). CHN analysis. Found: C, 30.38%; H, 2.62%; N, 5.11%. Calcd for C$_{21}$H$_{22}$ClF$_6$IN$_3$OsP: 0, 30.99%; H, 2.72%; N, 5.16%.

(FY069) [Os(η$^6$-bip)(2-F-azpy)I]PF$_6$.

[Os(η$^6$-bip)I$_2$]$_2$ (25.0 mg, 0.021 mmol) was dissolved in methanol (20 mL) at 313 K. 2-F-Azpy (8.4 mg, 0.042 mmol) in methanol (10 mL) was added drop-wise, the solution-color changed from yellow to brown immediately. The solution was heated under reflux (353K) for 12 h. The volume was reduced to about 10 mL by removal of methanol on a rotary evaporator, and ammonium hexafluorophosphate (13.7 mg. 0.084 mmol) was added. The solution was then left in the freezer (253K) for 24 h. Dark colored powder was precipitated which was collected by filtration, washed with cold ethanol and diethyl ether, then finally dried in vacuum. Yield: 15.5 mg (45.0%). ESI-MS Calcd for $C_{23}H_{15}FIN_3Os$: m/z 674.0. found 674.1. $^1H$ NMR $((CD_3)_2CO)$: δ 9.50 (t, 1H, J=2 Hz), 8.88 (d of d, 1H), 8.91 (d of d, 2H), 8.32 (d of t, 1H), 8.02 (d of d, 1H), 7.95-7.92 (m, 2H), 7.73-7.41 (m, 5H), 7.13-7.09 (m, 2H), 6.96 (t, 1H, J=7 Hz). 6.79 (d, 1H, J=7 Hz), 6.65 (t, 1H, J=7 Hz). CHN analysis. Found: C, 34.17%; H, 2.28%; N, 5.04%. Calcd for $C_{23}H_{18}F_7IN_3OsP$: C, 33.79%; H, 2.22%; N, 5.14%.

(FY078) $[Os(\eta^6\text{-bip})(2\text{-Cl-azpy})I]PF_6$.

$[Os(\eta^6\text{-bip})I_2]_2$ (30.0 mg, 0.025 mmol) was dissolved in methanol (10 mL) at 353 K and heated under reflux for 1 h. 2-Cl-azpy (10.8 mg, 0.050 mmol) in methanol (10 mL) was added drop-wise. The solution was stirred at 353 K for 2 h. The volume was reduced to about 10 mL by removal of methanol on a rotary evaporator, and ammonium hexafluorophosphate (16.3 mg. 0.10 mmol) was added. The solution was then left in the freezer (253K) for 24 h. Dark colored crystalline was precipitated which was collected by filtration, washed with cold ethanol and diethyl ether, then finally dried in vacuum. Yield: 24.5 mg (29.3%). ESI-MS Calcd for $C_{23}H_{18}ClIN_3Os$: m/z 690.0. found 689.9. $^1H$ NMR $((CD_3)_2CO)$: δ 9.46 (d, 1H, J=3 Hz), 8.99 (d, 1H, J=9 Hz), 8.40 (d of d, 1H), 7.91 (d, 2H, J=8 Hz), 7.69 (t, 1H, J=8 Hz), 7.55-7.47 (m, 3H), 7.44-7.39 (m, 4H), 7.13 (d, 1H, J=6 Hz), 7.09 (t, 1H, J=6 Hz), 6.89 (t, 1H, J=6 Hz), 6.82 (d, 1H, J=6 Hz), 6.72 (t, 1H, J=6 Hz). CHN analysis. Found: C, 32.92%; H, 2.06%; N, 5.03%. Calcd for $C_{23}H_{18}ClF_6IN_3OsP$: C, 33.21%; H, 2.18%; N, 5.04%.

(FY061) $[Os(bip)(2\text{-Br-azpy})I]PF_6$.

$[Os(bip)I_2]_2$ (30.0 mg, 0.025 mmol) was dissolved in methanol (30 mL) and water (10 mL), and the solution was heated under reflux (T=353 K) for 1.5 h. 2-Br-azpy (13.1 mg, 0.05 mmol) in methanol (10 mL) was added drop-wise, the solution-color changed from orange to brown immediately. The solution was stirred and heated under reflux for 1.5 h further. The volume was reduced to about 10 mL by removal of methanol on a rotary evaporator, and ammonium hexafluorophosphate (16.4 mg. 0.2 mmol) was added. The solution was then left in the fridge for 24 h. Dark colored powder was precipitated which was collected by filtration, washed with cold ethanol and diethyl ether, then finally dried in vacuum. Yield: 22.5 mg (51.2%). ESI-MS Calcd for $C_{23}H_{18}BrIN_3Os$: m/z 733.9. found 733.7. $^1H$ NMR $((CD_3)_2CO)$: δ 9.50 (d, 1H, J=2 Hz), 8.91 (d, 1H, J=9 Hz), 8.52 (d of d, 1H), 7.92 (d, 2H, J=8 Hz), 7.69 (t, 1H, J=8 Hz), 7.55-7.44 (m, 2H), 7.43-7.39 (m, 5H), 7.16-7.19 (m, 2H), 6.87 (t, 1H, J=6 Hz), 6.81 (d, 1H, J=6 Hz), 6.71 (t, 1H, J=6 Hz). CHN analysis. Found: C, 31.94%; H, 1.97%; N, 4.74%. Calcd for $C_{23}H_{18}BrF_6IN_3OsP$: C, 31.45%; H, 2.07% N, 4.78%.

(FY070) $[Os(\eta^6\text{-bip})(2\text{-I-azpy})I]PF_6$.

$[Os(\eta^6\text{-bip})I_2]_2$ (26.0 mg, 0.022 mmol) was dissolved in methanol (20 mL) and water (5 mL), and the solution was heated under reflux (T=353 K) for 1 h. 2-Br-azpy (13.4 mg, 0.043 mmol) in methanol (5 mL) was added drop-wise, the solution-color changed from orange to brown immediately. The solution was stirred and heated under reflux for 1 h further. The volume was reduced to about 10 mL by removal of methanol on a rotary evaporator, and ammonium hexafluorophosphate (14.3 mg. 0.088 mmol) was added. The solution was then left in the fridge for 24 h. Dark colored powder was precipitated which was collected by filtration, washed with cold ethanol and diethyl ether, then finally dried in vacuum. Yield: 19.2 mg (52.0%). ESI-MS Calcd for $C_{23}H_{18}F_6IN_3Os$: m/z 781.9. found 781.8. $^1H$ NMR $((CD_3)_2CO)$: δ 9.54 (d, 1H, J=2 Hz), 8.74 (d, 1H, J=9 Hz), 8.64 (d of d, 1H), 7.92 (d, 2H, J=8 Hz), 7.70 (t, 1H, J=8 Hz), 7.52-7.46 (m, 3H), 7.44-7.41 (m, 4H), 7.15 (d, 1H, J=6 Hz), 7.09 (d, 1H, J=6 Hz), 6.83-6.78 (m, 2H), 6.69 (t, 1H, J=6 Hz). CHN analysis. Found: C, 29.90%; H, 1.87%; N, 4.51%. Calcd for $C_{23}H_{18}F_6I_2N_3OsP$: C, 29.85%; H, 1.96% N, 4.54%.

(FY067) $[Os(\eta^6\text{-p-cym})(2\text{-I-azpy})I]PF_6$.

$[Os(\eta^6\text{-p-cym})I_2]_2$ (25.0 mg, 0.022 mmol) was dissolved in methanol (40 mL) at 313 K. 2-I-Azpy (13.4 mg, 0.043 mmol) in methanol (10 mL) was added drop-wise, the solution-color changed from orange to blue immediately. The solution was stirred at ambient temperature for 4 h. The volume was reduced to about 10 mL by removal of methanol on a rotary evaporator, and ammonium hexafluorophosphate (14.0 mg. 0.086 mmol) was added. The solution was then left in the freezer (253K) for 24 h. Dark colored powder was precipitated which was collected by filtration, washed with cold ethanol and diethyl ether, then finally dried in vacuum. Yield: 27.4 mg (70.4%). ESI-MS Calcd for $C_{21}H_{22}F_6IN_3Os$: m/z 762.0. found 761.8. $^1H$ NMR $((CD_3)_2CO)$: δ 9.89 (s, 1H), 9.13 (m, 1H), 8.71 (d of d, 1H), 8.18 (m, 2H), 7.82-7.73 (m, 2H), 6.91 (d, 1H, J=6 Hz), 6.59 (d, 1H, J=6 Hz), 6.41 (d, 1H, J=6 Hz), 6.35 (d, 1H, J=6 Hz), 2.83 (s, 3H), 2.65-2.61 (m, 1H), 1.02 (d of d, 6H). CHN analysis. Found: C, 27.62%; H, 2.27%; N, 4.64%. Calcd for $C_{21}H_{22}F_6I_2N_3OsP$: C, 27.86%; H, 2.45% N, 4.64%.

(FY052) $[Os(\eta^6\text{-bip})(3\text{-Cl-Azpy})I]PF_6$.

$[Os(\eta^6\text{-bip})I_2]_2$ (30.0 mg, 0.025 mmol) in methanol (30 mL) and water (10 mL) was heated under refluxed (T=348 K) for 1.5 h. 3-Cl-Azpy (11.2 mg, 0.052 mmol) in methanol (10 mL) was added drop-wise. The solution colour changed from orange to dark red immediately, it was stirred at 348 K for 1.5 h. The volume was reduced to 10 ml ac by removal of methanol on a rotary evaporator and ammonium hexafluorophosphate (41.0 mg. 0.25 mmol) was added. Then the solution was left in the fridge for 24 h. A dark colour powder precipitated, which was filtered off, washed with cold methanol and diethyl ether, dried in vacuum. Yield: 28.4 mg (68.1%). Anal. ESI-MS Calcd for $C_{23}H_{18}ClIN_3Os$: m/z 690.0. found 689.9. $^1H$ NMR $((CD_3)_2CO)$ δ 9.41 (d, J=6 Hz), 9.14 (d, 1H, J=2 Hz), 7.96-7.90 (m, 3H), 7.74 (t, 1H, J=5 Hz), 7.59-7.41 (m, 7H), 7.13 (d, 1H, J=6 Hz), 7.05 (t, 1H, J=6 Hz), 6.92-6.85 (m, 2H), 6.74 (t, 1H, J=6 Hz). CHN analysis Found: C, 33.12%; H, 2.18%; N, 5.04%, Calcd for $C_{23}H_{18}ClF_6IN_3OsP$: C, 32.89%; H, 2.89%; N, 5.48%.

(FY043) $[Os(\eta^6\text{-p-cym})(Abpy)I]PF_6$.

$[Os(\eta^6\text{-p-cym})I_2]_2$ (40.0 mg, 0.035 mmol) was dissolved in 50 mL of methanol at 313 K; Abpy (16.1 mg, 0.087 mmol) in methanol (5 mL) was added drop-wise, the solution colour changed from orange to pink immediately; it was stirred at ambient temperature for 16 h. The volume was reduced to 10 ml ca by removal of methanol on a rotary evaporator. Ammonium hexafluorophosphate (56.2 mg. 0.35 mmol) was added. Then the solution was left in the freezer (253K) for 24 h. A dark colour precipitate formed, which was filtered off, washed with cold ethanol and diethyl ether, then finally dried in vacuum. Yield: 35.2 mg (64.5%). Anal. ESI-MS Calcd for $C_{20}H_{22}IN_4Os$: m/z 637.0. found 637.0. H NMR $((CD_3)_2CO)$ δ 9.74 (d, 1H, J=6 Hz), 9.12 (m, 1H), 8.90 (d, 1H, J=5 Hz), 8.41 (m, 1H), 8.22 (m, 2H), 7.86 (m, 2H), 6.78 (d, 1H, J=6 Hz), 6.72 (d, 1H, J=6 Hz), 6.57 (d, 1H, J=6 Hz), 6.51 (d, 1H, J=6 Hz), 2.72 (s, 3H), 2.39 (m, 1H), 0.93 (d of d, 6H). CHN analysis Found: C, 30.91%; H, 2.74%; N, 7.28%, Calcd for $C_{20}H_{22}F_6IN_4OsP$: C, 30.78%; H, 2.84%; N, 7.18%.

(FY036) [Os($\eta^6$-p-cym)(OH-Azpy-NO$_2$)I]PF$_6$.

[Os($\eta^6$-p-cym)I$_2$]$_2$ (23.8 mg, 0.020 mmol) was dissolved in methanol (30 mL). OH-Azpy-NO$_2$ (10.5 mg, 0.043 mmol) in methanol (5 mL) was added drop-wise. The solution was stirred at ambient temperature for 48 h with 7 drops of HCl (1 M). The volume was reduced to 2 ml ac by removal of methanol on a rotary evaporator. The complex was purified by chromatography on a Sephadex LH20 column. Ammonium hexafluorophosphate (10.0 mg. 0.61 mmol) was added. Then the solution was left in the fridge for 0.5 h. A dark colour precipitate was filtered off, washed with cold ethanol and diethyl ether, then finally dried in vacuum. Yield: 12.7 mg (37.8%). Anal. ESI-MS Calcd for $C_{21}H_{22}IN_4O_3Os$: m/z 697.0. found 696.9. $^1$H NMR ((CD$_3$)$_2$CO) δ 9.87 (d, 1H, J=2 Hz), 9.68 (d, 1H, J=9 Hz), 9.39 (d, 2H, J=9 Hz), 9.73 (d, 2H, J=9 Hz), 8.57 (m, 1H), 7.38 (d, 1H, J=8 Hz), 7.04 (d, 1H, J=8 Hz), 6.57 (s, 1H), 4.50 (m, 1H), 3.60 (s, 3H), 1.86 (d of d, 6H). CHN analysis Found: C, 31.06%; H, 2.83%; N, 6.44%, Calcd for $C_{21}H_{22}F_6IN_4O_3OsP$: C, 30.01%; H, 2.64%; N, 6.67%.

(FY033) [Os($\eta^6$-p-cym)(OH-Azpy-NO$_2$)Cl]PF$_6$.

[Os($\eta^6$-p-cym)Cl$_2$]$_2$ (31.5 mg, 0.040 mmol) was dissolved in methanol (30 mL). OH-Azpy-NO$_2$ (19.7 mg, 0.081 mmol) in methanol (10 mL ac) was added drop-wise, the solution colour changed from yellow to brown immediately. The solution was stirred at ambient temperature for 4 h. The volume was reduced to about 2 ml by removal of methanol on a rotary evaporator. The complex was purified by chromatography on a Sephadex LH20 column. Ammonium hexafluorophosphate (26.2 mg. 0.16 mmol) was added. Then the solution was left in the freezer (253K) for 1 h; Dark colour powders precipitated which were filtered off, washed with diethyl ether, finally dried in vacuum. Yield: 25.1 mg (41.8%). Anal. ESI-MS Calcd for $C_{21}H_{22}ClN_4O_3Os$: m/z 605.1. found 605.1. $^1$H NMR ((CD$_3$)$_2$CO) δ 9.06 (d, 1H, J=2 Hz), 8.79 (d, 1H, J=9 Hz), 8.56 (d, 2H, J=9 Hz), 8.33 (d, 2H, J=9 Hz), 7.80 (d, 1H, J=8 Hz), 6.74 (d, 1H, J=8 Hz), 6.36 (d, 2H, J=8 Hz), 6.22 (d, 1H, J=8 Hz), 2.57-2.52 (m, 1H), 2.47 (s, 3H), 1.00 (d of d, 6H). CHN analysis Found: C, 34.35%; H, 2.95%; N, 7.35%, Calcd for $C_{21}H_{22}ClF_6N_4O_3OsP$: 0, 33.67%; H, 2.96%; N, 7.48%.

(FY175A) [($\eta^6$-p-cym)Os(Imine-S)I]PF$_6$.

[($\eta^6$-p-cym)OsI$_2$]$_2$ (50.0 mg, 0.043 mmol) was dissolved in methanol (20 mL) at 313 K. Imine-S (19.3 mg, 0.086 mmol) in methanol (10 mL) was added drop-wise, the solution-colour changed from orange to red immediately. The solution was stirred at ambient temperature for 24 h. Ammonium hexafluorophosphate (28.0 mg. 0.17 mmol) was added. Then the solution was left in the fridge for 24 h. Dark colour crystals was precipitated which was collected by filtration, washed with cold ethanol and diethyl ether, then finally dried in vacuum. Yield: 47.8 mg (67.7%). $^1$H NMR ((CD$_3$)$_2$CO): δ 9.57 (d, 1H, J=6 Hz), 9.43 (s, 1H), 8.48 (d, 1H, J=8 Hz), 8.25 (t, 1H, J=6 Hz), 7.77 (t, 2H, J=6 Hz), 7.52-7.48 (m, 3H), 6.49 (d, 1H, J=6 Hz), 6.26 (d, 1H, J=6 Hz), 6.08 (qd, 1H, J=6 Hz), 6.04 (d, 1H, J=6 Hz), 5.83 (d, 1H, J=6 Hz), 2.84 (s, 3H), 2.67-2.602 (m, 1H), 2.65 (s, 6H), 2.13 (d, 3H, J=7 Hz), 1.02 (d of d, 6H, J=7 Hz.

(FY178A) [($\eta^6$-p-cym)Os(Imine-R)I]PF$_6$.

[($\eta^6$-p-cym)OsI$_2$]$_2$ (50.0 mg, 0.043 mmol) was dissolved in methanol (20 mL) at 313 K. Imine-R (19.3 mg, 0.086 mmol) in methanol (10 mL) was added drop-wise, the solution-colour changed from orange to red immediately. The solution was stirred at ambient temperature for 24 h. Ammonium hexafluorophosphate (28.0 mg. 0.17 mmol) was added. Then the solution was left in the fridge for 24 h. Dark colour crystals was precipitated which was collected by filtration, washed with cold ethanol and diethyl ether, then finally dried in vacuum. Yield: 50.4 mg (71.3%). $^1$H NMR ((CD$_3$)$_2$CO): δ 9.57 (d, 1H, J=6 Hz), 9.43 (s, 1H), 8.48 (d, 1H, J=8 Hz), 8.25 (t, 1H, J=6 Hz), 7.77 (t, 2H, J=6 Hz), 7.52-7.48 (m, 3H), 6.49 (d, 1H, J=6 Hz), 6.26 (d, 1H, J=6 Hz), 6.08 (qd, 1H, J=6 Hz), 6.04 (d, 1H, J=6 Hz), 5.83 (d, 1H, J=6 Hz), 2.84 (s, 3H), 2.67-2.602 (m, 1H), 2.65 (s, 6H), 2.13 (d, 3H, J=7 Hz), 1.02 (d of d, 6H, J=7 Hz).

Structure-Activity Relationships:

Structure activity studies show that:

(1) iodide as the monodentate ligand showed an improved anticancer activity over chloride, iodide complexes tested so far are on average are 25 times more active in vitro (2) when biphenyl is the arene, the complexes are in general about 10 times more active than para-cymene complexes.

2-NCI Data of IC$_{50}$ and Compare Analysis:

Osmium compound: [Os($\eta^6$-p-cym)(azpy-NMe$_2$)I]PF$_6$ (FY026)

| Compound | GI$_{50}$/μM | TGI/μM | LC$_{50}$/μM |
|---|---|---|---|
| [Os($\eta^6$-p-cym)(azpy-NMe$_2$)I]PF$_6$ (FY026) | 0.28 | 1.17 | 6.3 |
| Cisplatin | 10.3 | 50.7 | 90.5 |

Cisplatin Data from NCI/DTP screening: October 2009, 48 h incubation.
[Os($\eta^6$-p-cym)(azpy-NMe$_2$)I]PF6 (FY026) was selected for study for activity towards the human tumor 60-cell line panel of the Developmental Therapeutics Program of the National Cancer Institute which includes nine tumor type subpanels.

The cells were treated for 48 h at five concentrations ranging from 0.01 to 100 μM. Three endpoints were calculated: GI 50 (the concentration inhibits cell growth by 50%): TGI (the concentration inhibits cell growth by 100%) LC 50 (the concentration kills original cells by 50%) MG-MID (full-panel mean-graph midpoint).

The results are shown in FIG. 10

[Os($\eta^6$-p-cym)(azpy-Nme$_2$)I]PF$_6$ showed a broad spectrum of activity, with MG-MID values much lower than those for cisplatin. It shows particular selectivity for leukemia, colon cancer, melanoma and breast cancer, and was particularly active against Leukemia HL-60 (TB), Leukemia MOLT-4 and colon cancer OoLO 205 giving GI 50 values less than 50 nM.

COMPARE Results Using the NCI/DTP Standard Agents Database

| Compound | Endpoint | Correlation | Name | Mechanism | Cisplatin |
|---|---|---|---|---|---|
| [Os($\eta^6$-p-cym)(azpy-NMe$_2$)I]PF$_6$ | GI$_{50}$ | 0.787 | Vinblastine sulfate | Antimicrotubule agent | −0.356 |
| | TGI | 0.813 | Vinblastine sulfate | Antimicrotubule agent | −0.291 |
| | LC$_{50}$ | 0.54 | Vinblastine sulfate | Antimicrotubule agent | −0.258 |

To gain insight into a possible mechanism of action [Os(η⁶-p-cym)(azpy-Nme₂)I]PF₆, a COMPARE analysis was carried out against the NCI/DTP Standard Agents database, a collection of 171 known anticancer compounds. The three endpoints (GI50, TGI, and LC50).

The molecule with the best correlation [Pearson correlation coefficient (PCC)] is vinblastine sulfate and the values for comparison with cisplatin are also given. The best PCCs for each endpoint belong to vinblastine sulfate which inhibit tubulin polymerization.

The Compare-negative score for cisplatin shows that the mechanism of action is totally different from cisplatin.

Inhibition of Tubulin Polymerization.

| Osmium Compounds at 10 µM | Inhibition of Tubulin Polimerziation/% |
|---|---|
| [Os(η⁶-bip)(1-CF₃-4-Cl-Azpy)I]PF₆ | 13.0 |
| [Os(η⁶-bip)(1-Cl-Azpy)I]PF₆ | 11.4 |
| [Os(η⁶-bip)(2-F-Azpy)I]PF₆ | 21.0 |
| [Os(η⁶-p-cym)(Azpy-NMe₂)I]PF₆ | 28.6 |

Prevention of Polymerization of Microtubules In Vitro.

To follow the anticancer mechanism indicated by COMPARE, We have investigated whether osmium complexes can interacted directly with tubulin. We incubated purified, unpolymerized tubulin with osmium compounds and monitored the polymerization process at 37° C. for 60 min, It was found that [Os(η⁶-bip)(2-F-Azpy)I]PF₆ reduced the amount of tubulin polymerized in a dose-dependent manner, whereas the best inhibitor [Os(η⁶-bip)(2-F-Azpy)I]PF₆ showed a IC₅₀ of tubulin polymerization at ca. 20 µM [not clear to me where compound [Os(η⁶-bip)(2-F-Azpy)I]PF₆ comes from]. All the other inhibition rates were also listed, [Os(η⁶-p-cym)(Azpy-NMe₂)I]PF₆ showed the best potential of inhibit tubulin polymerization which is consisted with results of COMPARE.

[Os(η⁶-bip)(2-F-Azpy)I]PF₆ Depolymerizes Microtubules in A2780 Human Ovarian Cancer Cell Line.

We observed an anti-proliferation effect after the 24 h treatment of [Os(η⁶-p-cym)(Azpy-NMe₂)I]PF₆. Most cells have long microtubule fragments scattered throughout the cytoplasm in the control cells, the inhibition forming microtubules were observed at low concentrations at 1 µM.

Tubulin Polymerization Assay.

A Cytoskeleton tubulin polymerization assay kit (catalog no BK004) was used in the tubulin polymerization study. Briefly, 10 µL of general tubulin buffer (80 mM PIPES, pH 6.9, 2 mM MgCl₂, and 0.5 mM EGTA) containing osmium compound, colchicine or taxol was pipetted into the prewarmed 96 well microplate. Tubulin (defrosted to room temperature from −80° C. and then placed on ice before use) was diluted with tubulin polymerization buffer with 1 mM GTP to a final concentration of 4 mg mL⁻¹. Diluted tubulin (100 µL) was added into the wells containing osmium compound, colchicine or taxol. Diluted tubulin (100 µL) mixed with general tubulin buffer (10 µL) served as control. The absorbance at 340 nm was read immediately with a Tecan microplate reader.

Immunofluresence by Confocal Microscopy.

A2780 Cells were seeded on Lab-Tek™ Chamber Slides (Thermo Scientific Nunc) 10,000 cells/chamber, after 24 h incubation, osmium compound [Os(η⁶-bip)(2-F-Azpy)I]PF₆ at different concentrations were added and incubate for another 24 h. Cells were fixed with 4% formaldehyde in PBS (20 min, 310 K), then rinsed with PBS (3×2 mL×2 min), and permeabilized with 0.1% Triton X-100 solution (PBS solution) for 15 min at ambient temperature. The cells were blocked with blocking buffer (2 mg/mL BSA, overnight at 269 K), and then, the cell monolayers were incubated (1 h, 310 K) with monoclonal anti-α-tubulin-Alexa 488 (4 µg/mL) (Invitrogen Molecular Probles, Catalog No. 32-2588). After the incubation, the cells were washed with PBS and the immunofluorescence was detected using a Leica SP5 fluorescence confocal microscope, with 100× objective.

In Vivo Studies

We studied the anticancer efficacy of complex [Os(η⁶-p-cym)(Azpy-NMe₂)I]PF₆ in vivo versus the subcutaneously implanted HCT-116 xenograft model [Biochemical Pharmacology, 68, 2004, 2107-16], when administered as a single intravenous injection at its maximum soluble dose of 40 mg/kg. The agent had negligible toxicity, with an observed maximum weight loss well within the normal limits. Complex [Os(η⁶-p-cym)(Azpy-NMe₂)I]PF₆ was seen to induce a statistically significant tumour growth delay in the HCT-116 model compared to the untreated control (p<0.01), and positive control compound, the standard agent cisplatin (p<0.05) see table below. The lack of toxicity seen, combined with the favourable tumour distribution, would suggest that there is significant scope to administer this compound on a repeat-dose schedule to enhance its therapeutic ability. We have also shown similar results when the osmium compound is administered in 4 separate 10 mg/kg doses Evaluation of the in vivo efficacy of [Os(η⁶-p-cym)(Azpy-NMe₂)I]PF₆ in the HCT-116 colon adenocarcinoma s.c. xenograft model

| Compound (dose in mg kg⁻¹) | Median tumour doubling time (days) | Significance | Maximum % weight loss (day) |
|---|---|---|---|
| Untreated controls | 3.9 | | 8 (8) |
| [Os(η⁶-p-cym)(Azpy-NMe₂)I]PF₆ (40.0) | 6.2 | p < 0.01 | 8 (1) |
| Cisplatin (8.0) | 6.4 | p = 0.05 | 8 (6) |

Chart 1. Osmium Azo- and Imino-Pyridine Arene Complexes Studied in this Work.

This needs to be updated. The revised chart in the draft paper does not include the imine compounds and so I cannot simply replace.

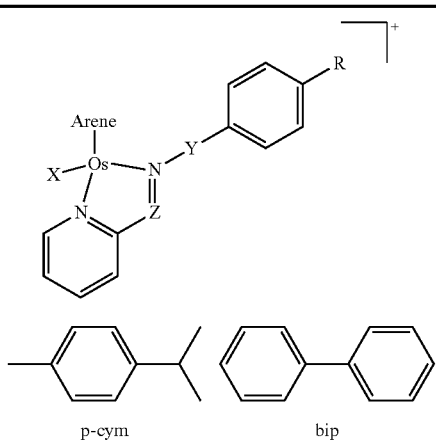

p-cym     bip

The complexes listed below all have Y absent:

| Complex | Arene | R | X | Z |
|---|---|---|---|---|
| 1 | bip | H | I | N |
| 2 | p-cym | H | I | N |
| 3 | bip | OH | I | N |
| 4 | p-cym | OH | I | N |
| 5 | bip | NMe$_2$ | I | N |
| 6 | p-cym | NMe$_2$ | I | N |
| 7 | bip | H | Cl | N |
| 8 | p-cym | H | Cl | N |
| 9 | bip | OH | Cl | N |
| 10 | p-cym | OH | Cl | N |
| 11 | bip | NMe$_2$ | Cl | N |
| 12 | p-cym | NMe$_2$ | Cl | N |
| 13 | p-cym | NMe$_2$ | I | CH |
| 14 | bip | H | I | CH |
| 15 | p-cym | H | Cl | CH |
| 16 | p-cym | NMe$_2$ | I | CH |

Azopyridine lgand abbreviations take the form:
R = NMe$_2$: Azpy-NMe$_2$ etc
For iminopyridine ligands:
R = NMe$_2$: pp-NMe$_2$, etc

TABLE 1(A)

IC$_{50}$ values for azopyridine complexes against A2780 ovarian cancer cells

| Complex | IC$_{50}$ (μM) |
|---|---|
| [(η$^6$-bip)Os(Azpy)I]PF$_6$ (1) | 5.4 |
| [(η$^6$-p-cym)Os(Azpy)I]PF$_6$ (2) | 10.2 |
| [(η$^6$-bip)Os(Azpy-OH)I]PF$_6$ (3) | 0.14 |
| [(η$^6$-p-cym)Os(Azpy-OH)I]PF$_6$ (4) | 0.3 |
| [(η$^6$-bip)Os(Azpy-NMe$_2$)I]PF$_6$ (5) | 0.14 |
| [(η$^6$-p-cym)Os(Azpy-NMe$_2$)I]PF$_6$ (6) | 0.2 |
| [(η$^6$-bip)Os(Azpy)Cl]PF$_6$ (7) | 13.9 |
| [(η$^6$-p-cym)Os(Azpy)Cl]PF$_6$ (8) | >50 |
| [(η$^6$-bip)Os(Azpy-OH)Cl]PF$_6$ (9) | 0.8 |
| [(η$^6$-p-cym)Os(Azpy-OH)Cl]PF$_6$(10) | 1.3 |
| [(η$^6$-bip)Os(Azpy-NMe$_2$)Cl]PF$_6$ (11) | 3.9 |
| [(η$^6$-p-cym)Os(Azpy-NMe$_2$)Cl]PF$_6$ (12) | 1.8 |
| Cisplatin | 2 |

TABLE 1 (B)

IC$_{50}$ values for iminopyridine complexes against A2780 ovarian cancer cells

| Complex | IC$_{50}$ (μM) |
|---|---|
| 13[(η$^6$-p-cym)Os(pp-NMe$_2$)I]PF$_6$ | 0.4 |
| 14[(η$^6$-bip)Os(pp)I]PF$_6$ | 18.6 |
| 15[(η$^6$-p-cym)Os(pp)Cl]PF$_6$ | 26.2 |
| 16[(η$^6$-p-cym)Os(pp-NMe$_2$)Cl]PF$_6$ | 3.5 |
| Cisplatin | 2 |

TABLE 1(C)

(C) IC$_{50}$ Values for complexes 3, 12, 6 against A2780/cis, A549, HCT-116, MCF-7, PC-3 and RT-112 Cell Lines.

| Complex | A2780/cis | A549 | HCT-116 | MCF-7 | PC-3 | RT-112 |
|---|---|---|---|---|---|---|
| [(η$^6$-bip)Os(Azpy-OH)I]PF$_6$ (3) | <0.3 | 0.4 | <0.3 | 0.25 | <0.3 | 0.4 |
| [(η$^6$-p-cym)Os(Azpy-NMe$_2$)I]PF$_6$ (6) | <0.3 | <0.3 | <0.3 | 0.079 | 0.6 | <0.3 |
| [(η$^6$-p-cym)Os(Azpy-NMe$_2$)Cl]PF$_6$ (12) | 1.8 | 5.2 | 0.9 | 1.1 | 6.8 | 2.2 |
| Cisplatin | 4 | 4.1 | 2.6 | 3 | 21.5 | 1.4 |

TABLE 2

Selected Bond Lengths (Å) and Angles (deg) for [(η$^6$-p-cym)Os(Azpy)I]PF$_6$ (2), [(η$^6$-bip)Os(Azpy-O)I] (3*), [(η$^6$-bip)Os(Azpy-NMe$_2$)I]PF$_6$ (5), [(η$^6$-p-cym)Os(Azpy)Cl]PF$_6$ (8), [(η$^6$-bip)Os(Azpy-NMe$_2$)Cl]PF$_6$ (11).

(A)

| bond length/angle | 2 | 3 | 5 |
|---|---|---|---|
| Os(1)—N(8) | 2.010(3) | 2.080(2) | 2.1017(18) |
| Os(1)—N(1) | 2.052(3) | 2.054(2) | 2.0804(18) |
| Os(1)—C(15) | 2.186(3) | 2.206(3) | 2.189(2) |
| Os(1)—C(19) | 2.206(3) | 2.211(3) | 2.199(2) |
| Os(1)—C(18) | 2.225(3) | 2.211(3) | 2.205(2) |
| Os(1)—C(16) | 2.244(3) | 2.215(3) | 2.206(2) |
| Os(1)—C(20) | 2.246(3) | 2.217(3) | 2.211(2) |
| Os(1)—C(17) | 2.284(3) | 2.225(3) | 2.222(2) |
| Os(1)—I(1) | 2.6856(3) | 2.7185(2) | 2.70798(19) |
| N(7)—N(8) | 1.293(4) | 1.323(3) | 1.314(3) |
| N(8)—Os(1)—N(1) | 74.85(11) | 75.12(9) | 76.74(7) |
| N1—Os—I | 87.81(8) | 87.59(6) | 86.00(5) |
| I—Os—N8 | 83.07(8) | 87.83(6) | 86.60(5) |

(B)

| bond length/angle | 8 | 11 |
|---|---|---|
| Os(1)—N(8) | 2.0225(15) | 2.072(2) |
| Os(1)—N(1) | 2.0543(15) | 2.049(2) |
| Os(1)—C(15) | 2.1843(18) | 2.198(3) |
| Os(1)—C(19) | 2.2196(18) | 2.205(3) |
| Os(1)—C(18) | 2.2313(18) | 2.205(3) |
| Os(1)—C(16) | 2.2381(18) | 2.214(3) |
| Os(1)—C(20) | 2.2474(19) | 2.218(3) |
| Os(1)—C(17) | 2.2619(18) | 2.218(2) |
| Os(1)—Cl(1) | 2.3817(5) | 2.3992(6) |
| N(7)—N(8) | 1.290(2) | 1.297(3) |
| N(8)—Os(1)—N(1) | 74.84(6) | 75.23(9) |
| N1—Os—Cl | 84.35(5) | 85.12(6) |
| Cl—Os—N8 | 86.59(5) | 83.82(6) |

REFERENCES

1. Schaake-Koning, C.; van den Bogaert, W.; Dalesio, O.; Festen, J.; Hoogenhout, J.; van Houtte, P.; Kirkpatrick, A.; Koolen, M.; Maat, B.; Nijs, A.; et al. Effects of concomitant cisplatin and radiotherapy on inoperable non-small-cell lung cancer. *N Engl J Med* 1992, 326, 524-530.
2. Hartinger, C. G.; Zorbas-Seifried, S.; Jakupec, M. A.; Kynast, B.; Zorbas, H.; Keppler, B. K. From bench to bedside—preclinical and early clinical development of the anticancer agent indazolium trans-[tetrachlorobis(1H-indazole)ruthenate(III)] (KP1019 or FFC14A). *J. Inorg. Biochem* 2006, 100, 891-904.
3. Rademaker-Lakhai, J. M.; van den Bongard, D.; Pluim, D.; Beijnen, J. H.; Schellens, J. H. A Phase I and pharmacological study with imidazolium-trans-DMSO-imidazole-tetrachlororuthenate, a novel ruthenium anticancer agent. *CLIN CANCER RES* 2004, 10, 3717-27.
4. Wang, F.; Habtemariam, A.; van der Geer, E. P.; Fernandez, R.; Melchart, M.; Deeth, R. J.; Aird, R.; Guichard, S.; Fabbiani, F. P.; Lozano-Casal, P.; Oswald, I. D.; Jodrell, D. I.; Parsons, S.; Sadler, P. J. Controlling ligand substitution reactions of organometallic complexes: tuning cancer cell cytotoxicity. *Proc Natl Acad Sci* 2005, 102, 18269-74.
5. Aird, R. E.; Cummings, J.; Ritchie, A. A.; Muir, M.; Morris, R. E.; Chen, H.; Sadler, P. J.; Jodrell, D. I. In vitro and in vivo activity and cross resistance profiles of novel ruthenium (II) organometallic arene complexes in human ovarian cancer. *Br J Cancer* 2002, 86, 1652-7.
6. Peacock, A. F. A.; Parsons, S.; Sadler, P. J. Tuning the Hydrolytic Aqueous Chemistry of Osmium Arene Complexes with N,O-Chelating Ligands to Achieve Cancer Cell Cytotoxicity. *JACS* 2007, 129, 3348-3357.
7. van Rijt, S. H.; Hebden, A. J.; Amaresekera, T.; Deeth, R. J.; Clarkson, G. J.; Parsons, S.; McGowan, P. C.; Sadler, P. J. Amide Linkage Isomerism As an Activity Switch for Organometallic Osmium and Ruthenium Anticancer Complexes. *J. Med. Chem* 2009, 52, 7753-7764.
8. Peacock, A. F. A.; Habtemariam, A.; FernÃndez, R.; Walland, V.; Fabbiani, F. P. A.; Parsons, S.; Aird, R. E.; Jodrell, D. I.; Sadler, P. J. Tuning the Reactivity of Osmium(II) and Ruthenium(II) Arene Complexes under Physiological Conditions. *JACS* 2006, 128, 1739-1748.
9. Dougan, S. J.; Melchart, M.; Habtemariam, A.; Parsons, S.; Sadler, P. J. Phenylazo-pyridine and Phenylazo-pyrazole Chlorido Ruthenium(II) Arene Complexes: Arene Loss, Aquation, and Cancer Cell Cytotoxicity. *Inorg. Chem* 2006, 45, 10882-10894.
10. *CrysAlisPro* 2007, 171, 5.
11. Sheldrick, G. M. *Acta Cryst* 1990, A46, 467-473.
12. Sheldrick, G. M. *SHELX97* 1997, Programs for Crystal Structure Analysis (Release 97-2); University of Göttingen, Germany.
13. Mosmann, T. Rapid colorimetric assay for cellular growth and survival: application to proliferation and cytotoxicity assays. *J. Immunol. Methods* 1983, 65, 55-63.
14. Peacock, A. F. A.; Habtemariam, A.; Moggach, S. A.; Prescimone, A.; Parsons, S.; Sadler, P. J. Chloro Half-Sandwich Osmium(II) Complexes: Influence of Chelated N,N-Ligands on Hydrolysis, Guanine Binding, and Cytotoxicity. *Inorg. Chem* 2007, 46, 4049-4059.
15. Dougan, S. J.; Habtemariam, A.; McHale, S. E.; Parsons, S.; Sadler, P. J. Catalytic organometallic anticancer complexes. *Proc Natl Acad Sci* 2008, 105, 11628-33.
16. Godbout, J. P.; Pesavento, J.; Hartman, M. E.; Manson, S. R.; Freund, G. G. Methylglyoxal enhances cisplatin-induced cytotoxicity by activating protein kinase Cdelta. *JBC* 2002, 277, 2554-61.

The invention claimed is:

1. A compound of formula (I):

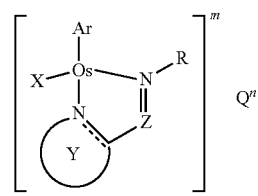

or a dinuclear or polynuclear form thereof, wherein

Ar is a benzene ring which may be optionally substituted by a branched or unbranched substituted or unsubstituted linear alkyl, a monocyclic or polycyclic aryl, hydroxyl or amino group;

X is Cl or I;

Y represents an unsaturated N-containing five or six membered ring;

Z is CR', where R' is H, CN, $N_3$, $C_1$-$C_{10}$ alkyl or aryl;

R is a substituted or unsubstituted phenyl;

when substituted the phenyl group is substituted on one or more carbons in the ring by OH, amino or substituted amino;

Q is an ion and is either present or absent;

m and n are charges, independently either absent or selected from a positive or negative whole number, or solvate, prodrug, physiologically active derivative, or solvolysis product thereof.

2. The compound according to claim 1, wherein Z is CH.

3. The compound according to claim 1, wherein X is I.

4. The compound according to claim 1, wherein Ar is biphenyl.

5. The compound according to claim 1, according to formula II

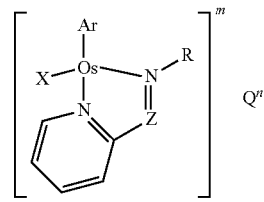

wherein Ar, X, R, Z, Q, m and n are as defined in claim 1, or a solvate, prodrug, physiologically active derivative, or solvolysis product thereof.

6. A compound according to formula (III)

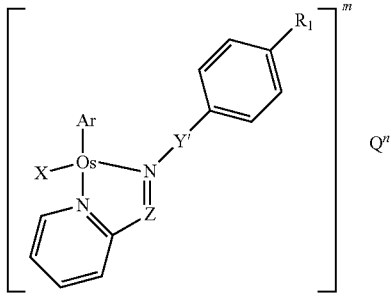

wherein X is a halo or a donor ligand, Q is an ion and is present or absent, and Ar is an arene moiety, Z is CH, $R_1$ is H, $C_1$-$C_4$ alkyl, OH, amino or substituted amino, carboxylate or substituted carboxylate, ether or polyether, nitro, halo, trifluoromethyl, or is another ring; Y is absent or is a C(R')(R") group in which R' and R" are independently H or a methyl group, m and n are charges, independently either absent or selected from a positive or negative whole number; or a solvate, prodrug, physiologically active derivative, or solvolysis product thereof.

7. The compound according to claim 6, wherein Z is CH, X is I, $R_1$ is OH, or $N(CH_3)_2$, R' and R" is H or methyl group independently and Q is $PF_6$ or another negatively charged counter ion.

8. A pharmaceutical composition comprising a compound according to claim 1 together with a pharmaceutically acceptable carrier thereof.

9. A method of treating cancer comprising administering, to a subject in need of such treatment, a therapeutically effective amount of a compound of formula (I):

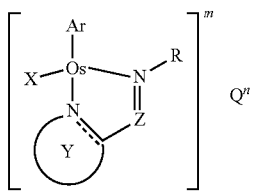

or a dinuclear or polynuclear form thereof, wherein
Ar is a benzene ring which may be optionally substituted by a branched or unbranched substituted or unsubstituted linear alkyl, a monocyclic or polycyclic aryl, hydroxyl or amino group;

X is Cl or I;
Y represents an unsaturated N-containing five or six membered ring;
Z is CR', where R' may be H, CN, $N_3$, $C_1$-$C_{10}$ alkyl or aryl;
R is a substituted or unsubstituted phenyl; when substituted the phenyl group is substituted on one or more carbons in the ring by OH, amino or substituted amino;
Q is an ion and is either present or absent;
m and n are charges, independently either absent or selected from a positive or negative whole member, or a solvate, prodrug, physiologically active derivative, or solvolysis product thereof.

10. A pharmaceutical composition comprising a compound according to claim 6 together with a pharmaceutically acceptable carrier thereof.

11. A method of treating cancer comprising administering, to a subject in need of such treatment, a therapeutically effective amount of a compound of formula (III)

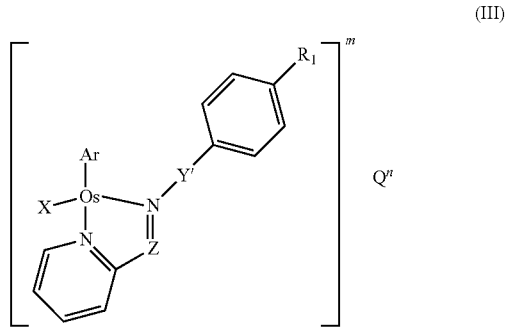

wherein X is halo or a donor ligand, Q is an ion and is present or absent, Ar is an arene moiety, Z is CH, $R_1$ is H, $C_1$-$C_4$ alkyl, OH, amino or substituted amino, carboxylate or substituted carboxylate, ether or polyether, nitro, halo, trifluoromethyl, or could be another ring; Y is absent or is a C(R')(R") group in which R' and R" are independently H or a methyl group, m and n are charges, independently either absent or selected from a positive or negative whole number;
or a solvate, prodrug, physiologically active derivative, or solvolysis product thereof.

* * * * *